(12) United States Patent
Masi et al.

(10) Patent No.: US 8,128,605 B2
(45) Date of Patent: Mar. 6, 2012

(54) SYRINGE FOR USE IN MEDICAL APPLICATIONS

(75) Inventors: Louis C. Masi, Greenland, NH (US); W. Scott Keeley, Charlestown, RI (US); Timothy Hickey, Chicopee, MA (US); Stanley Kowalski, III, Wilbraham, MA (US)

(73) Assignee: Mentor Worldwide LLC, Santa Barbara, CA (US)

( * ) Notice: Subject to any disclaimer, the term of this patent is extended or adjusted under 35 U.S.C. 154(b) by 35 days.

(21) Appl. No.: 12/341,186

(22) Filed: Dec. 22, 2008

(65) Prior Publication Data
US 2009/0270814 A1    Oct. 29, 2009

Related U.S. Application Data

(60) Provisional application No. 61/009,123, filed on Dec. 24, 2007, provisional application No. 61/009,120, filed on Dec. 24, 2007, provisional application No. 61/009,116, filed on Dec. 24, 2007, provisional application No. 61/009,122, filed on Dec. 24, 2007.

(51) Int. Cl.
*A61M 5/00*    (2006.01)
*A61M 5/315*   (2006.01)

(52) U.S. Cl. ........ 604/240; 604/227; 604/187; 604/181; 604/188; 604/218

(58) Field of Classification Search .......... 604/190, 604/197, 227, 240, 36, 232, 566, 165.01, 604/110, 198
See application file for complete search history.

(56) References Cited

U.S. PATENT DOCUMENTS

| | | | | |
|---|---|---|---|---|
| 2,691,372 A * | 10/1954 | Lores | ............. | 604/201 |
| 3,493,503 A * | 2/1970 | Mass | ............. | 210/778 |
| 4,013,080 A * | 3/1977 | Froning | ............. | 604/165.01 |
| 4,332,249 A * | 6/1982 | Joslin | ............. | 604/36 |
| 4,622,136 A * | 11/1986 | Karcey | ............. | 210/167.09 |
| 4,710,170 A * | 12/1987 | Haber et al. | ............. | 604/110 |
| 4,762,516 A * | 8/1988 | Luther et al. | ............. | 604/164.08 |
| 4,986,813 A * | 1/1991 | Blake et al. | ............. | 604/110 |
| 5,320,110 A * | 6/1994 | Wang | ............. | 600/566 |
| 5,336,186 A * | 8/1994 | Haber et al. | ............. | 604/110 |
| 5,593,391 A * | 1/1997 | Stanners | ............. | 604/232 |
| 5,665,075 A * | 9/1997 | Gyure et al. | ............. | 604/263 |
| 6,391,003 B1 * | 5/2002 | Lesch, Jr. | ............. | 604/110 |

FOREIGN PATENT DOCUMENTS
GB          2232599     *  8/1989
* cited by examiner

*Primary Examiner* — Kevin C Sirmons
*Assistant Examiner* — Bradley Thomas, Jr.

(57) ABSTRACT

A flow delivery system including a syringe that includes an outer plastic shell, a leur and a plunger; and a needle and/or a catheter that embodies a hub and a cannula which delivers a solution of a material. Various structures are included to provide locking engagements, torque sensitive connections, sufficient interfacing between components and visual conformation of connectors. The syringe assembly can also include an approach to a filter. Moreover, an approach to sterilization is provided.

10 Claims, 25 Drawing Sheets

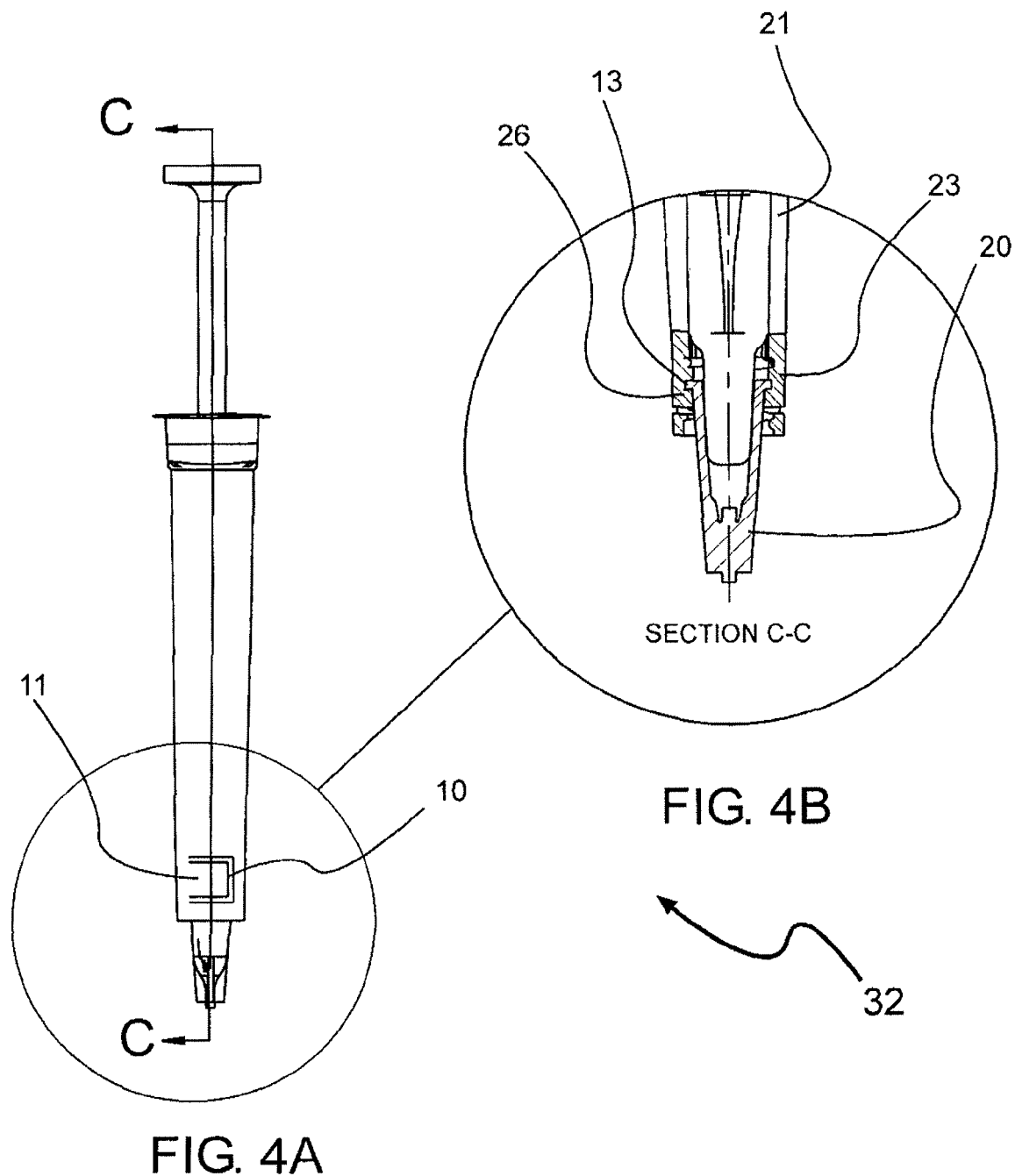

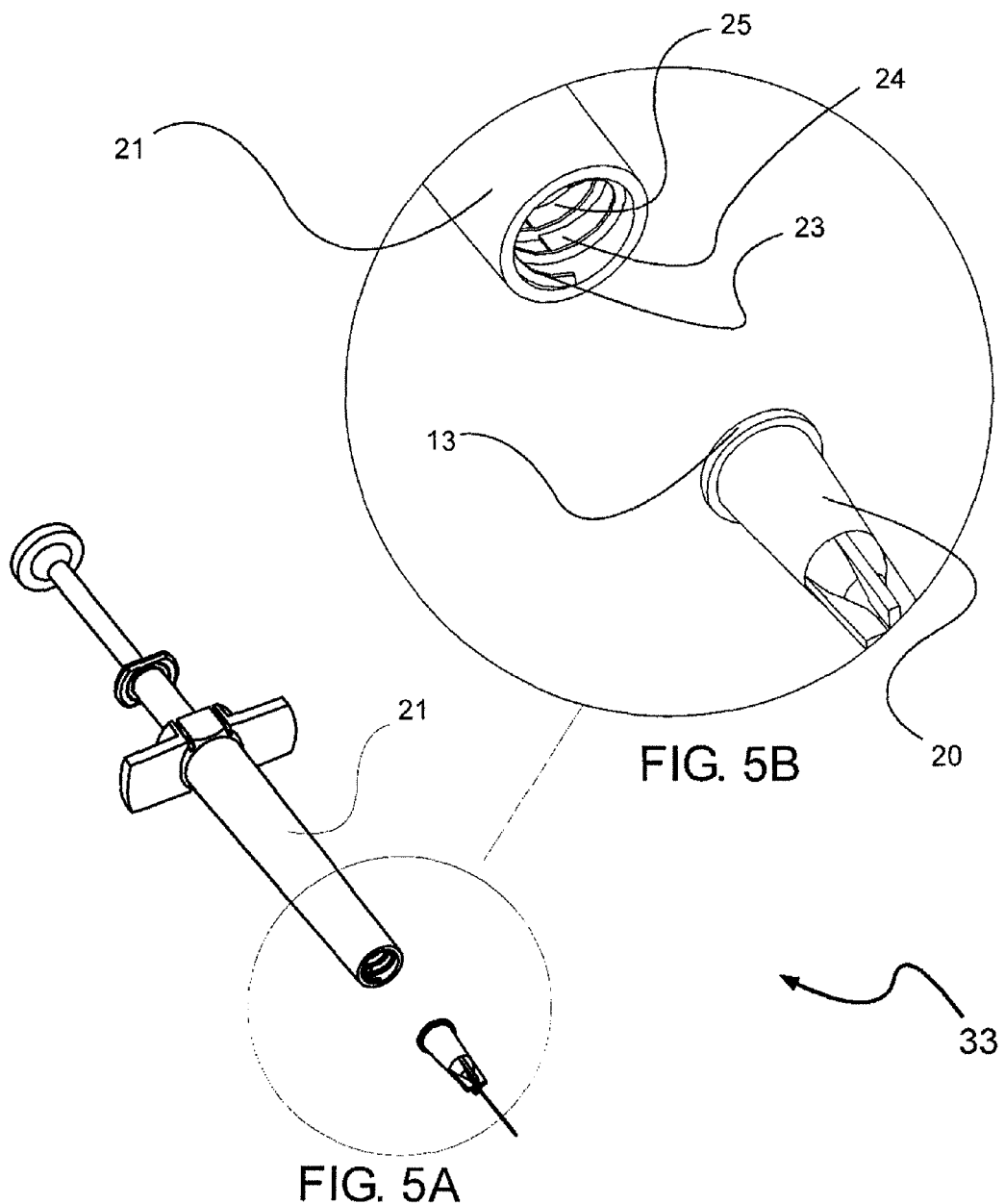

Section B-B

SYRINGE FOR USE IN MEDICAL APPLICATIONS

CROSS-REFERENCE TO RELATED APPLICATIONS

This application claims the benefit of U.S. Provisional Application No. 61/009,123, filed Dec. 24, 2007; U.S. Provisional Application No. 61/009,120, filed Dec. 24, 2007; U.S. Provisional Application No. 61/009,116, filed Dec. 24, 2007; and U.S. Provisional Application No. 61/009,122, filed Dec. 24, 2007; each of which are herein incorporated by reference in their entirety.

BACKGROUND

This disclosure relates in general to a flow delivery system that delivers material such as a biomaterial into a body, and in particular, to a syringe body for delivery of an aqueous solution containing a biomaterial or a mixture of a biomaterial and a biocompatible fluid lubricant.

This disclosure also relates to a flow delivery system, including a rotating grip or flange for the upper portion of the syringe. Needles on the syringes have a beveled distal end that creates a sharp point. The finger grips or flanges that allow the surgeon to position their index and middle finger on the body of the syringe while pushing the plunger with their thumb are commonly affixed to the syringe body. Some surgeons, including cosmetic and plastic surgeons, prefer to position the bevel in a specific direction, such as facing upward away from the skin or facing downward toward the skin depending on the procedure. When the finger grips are affixed to the syringe body, the surgeon must rotate the needle in order to configure the syringe so that the bevel on the needle is pointing in the desired direction. Many needles are engaged with the syringe body and leur by means of threads, and by rotating the needle, it is possible to loosen the connection between the needle and syringe body thus causing the needle to disengage under pressure. When disengaged while under pressure, the needle can launch from the distal end of the leur creating a sharp projectile.

The present disclosure further relates to shields for syringes such as a cover/container for a needle, also known as a cannula and hub assembly having a hub portion and a cannula portion. Moreover, the present disclosure is directed to an interface between the leur and the cannula as well as to the interface between the needle hub and the leur. Often a plenum results in the area where a needle assembly (cannula and hub) meets a syringe assembly (outer shell and leur). Certain situations can develop in which pressure builds up in the plenum and can cause a needle tip to become disengaged from the leur. When caused to disengage while under pressure, the cannula and hub assembly can launch from the distal end of the leur creating a sharp projectile.

Moreover, this disclosure concerns a system that includes a filter that breaks up or downsizes particles of material that are larger than desired (e.g., a relatively large agglomerated mass of the particles) for more effective delivery of the aqueous solution into the body.

Medical procedures often involve the non-surgical implanting of biomaterials into the body. An example is the injecting of a dermal filler material such as collagen through the use of a syringe and needle. The biomaterial can be solid and load-bearing and is typically suspended as an aqueous solution of the biomaterial particles. The solution is then injected with a syringe through a needle. For precise placement of materials into the facial dermis, a very fine cannula, e.g. 27 gauge (0.0075" inside diameter or ID) to 30 gauge (9.0055" ID), is preferred. These relatively small ID cannulas limit the diameter of the suspended particles that may pass through the cannula orifice during product delivery. The diameter of the particles of a product will typically range from 1-20 microns (0.001 mm-0.02 mm) in length and less than 20 microns (0.02 mm) in width. Products including larger particles can have diameters in the range of 200-700 and up to 1000 microns. In general, smaller particles can be less deformable than larger particles. Moreover, the particles can be generally spherical initially and then assume non-spherical profiles during product delivery through a cannula. It has been determined that larger particles are desirable in some situations, such as for the containment of time release medication. The larger particles pose a problem when used with the smaller cannulas required in the facial derma. The larger particles can bridge or agglomerate, resulting in clogging of the small orifice cannula. Larger particles also result in a greater amount of force needed to translate the syringe plunger especially where the particles are relatively less deformable. Common syringes include a central vessel (or leur) engaged with an outer shell, a plunger and a needle. The needle can embody a cannula that is engaged with a cone shaped portion, (or hub) that is press-fit onto the leur. Various mechanical structures such as threading are employed to assist in the press fit of the cannula and hub on to the leur. A plenum resides between the exit orifice of the leur and the entrance orifice of the cannula. When material agglomerates in this plenum, and the user will tend to increase pressure on the plunger, this higher force has a tendency to be sufficient to cause the cannula and hub assembly to launch out of the syringe.

There has been substantial research and experimentation in various mechanical methods for securing a needle tip to a syringe. U.S. Pat. No. 6,613,022 B1 is a passive needle guard that includes a body having a cavity to hold a syringe. U.S. Pat. No. 7,160,311 B2 is a compression plate apparatus that enables vessels to be joined together in various configurations. U.S. Pat. No. 7,214,207 B2 is a therapeutic infusion assembly for the subcutaneous delivery of a fluid from a remote source. U.S. Pat. No. 7,214,227 B2 is a closure member, such as a set screw and complementary receiving member included in a medical implant device. U.S. Pat. No. 7,274,966 B2 is a medical fluid delivery system including an implantable medical lead including a fixation element adapted to secure the lead to a tissue site and a fluid delivery device including a tissue piercing distal tip. U.S. Pat. No. 7,250,036 is a method for using a needle assembly for intradermal injection and a drug delivery device. U.S. Pat. No. 6,520,935 is a tip cap assembly for positive sealing engagement with a tip of syringe barrel of a syringe. U.S. patent application No. 20070255225 An intradermal needle comprising a needle cannula assembly having a limiter portion, a hub portion and a needle cannula, a protective cap having a forward and rearward cap to protect and shield a needle cannula prior to an after use, and means for engaging the needle cannula assembly and the rearward cap after use. U.S. patent application No. 20070149924 is a needle assembly including a cover, an inner shield, a needle and a hub assembly is provided. After use, the cover is placed over the distal (patient) end of the needle and the inner shield can be used to cover the proximal (non-patient) end of the needle. U.S. patent application No. 20050004552 is a passive shield system for a syringe including a body, shield, spring and ring which provide an interlock of the shield in the retracted position prior to receipt of the syringe for bulk transportation and processing and wherein the user selects the timing of the release of the shield to its extended position following injection, but which assures shielding of the syringe needle following release of the syringe plunger. U.S. patent application No. 20040102740 is a safety needle includes a needle with a sharp end and a needle shield. The needle shield includes collapsible interlocking members. U.S. patent application No. 20040097882 is a shield that protects the needle of a syringe and maintains it in a sterile condition until use. As stated, larger particles bridging or agglomerating resulting in clogging of the small orifice needle, thus resulting in a greater amount of force needed to translate the syringe plunger, the higher force may cause the surgeon to tremble and slight perturbations of the hand could result. Therefore, it is desirable to have applied forces equivalent to a low viscosity Newtonian fluid.

Other applications for implanting a biomaterial into the human body include use of the biomaterial as a bulking or augmenting agent in internal body tissue, such as the tissue that defines various sphincters, for example, in the urinary tract (specifically, in the urinary outflow of the bladder into the urethra) or in the lower esophageal area connecting the esophagus to the stomach. The malfunctioning of these sphincters is usually in the form of improper or incomplete closure of the sphincters, which leads to medical conditions such as urinary incontinence and gastroesophageal reflux disease (GERD) or heartburn, respectively. Treatment of these medical conditions may include injections of a viscous material dispersed in a solution, such as collagen, in the vicinity of the associated sphincter to augment or bulk up and fortify the tissue and thereby assist in the adequate closure of the corresponding sphincter for re-establishment of normal sphincter control. Still other applications for implanting a biomaterial such as collagen into the human body include various other body passages and tissues; for example, for correcting wrinkles not only in the facial derma but in other areas of the body as well.

In these applications it is known to inject the biomaterial, typically suspended in an aqueous solution, into the human body through use of a syringe together with an elongate needle and/or catheter. This type of flow delivery system may be used as a stand alone device or in combination with an appropriate medical instrument, such as a cystoscope, endoscope or gastroscope, which instruments are utilized to view the tissue in the affected area. However, as the length of the elongate needle and/or catheter increases, the amount of the force required to properly deliver the suspended mass aqueous solution of biomaterial to the desired body tissue area also increases. With known flow delivery systems, this increased amount of required force can cause problems both with the extrusion of the biomaterial through the flow delivery system and also with the intrusion of the biomaterial into the tissue. Oftentimes poor intrusion into the body tissue is the result of poor extrusion through the flow delivery system.

There also has been substantial research and experimentation in various chemical compositions to reduce plunger force in a syringe and needle and/or catheter flow delivery system. An area commonly researched is the ability to introduce lubricity between the particles through use of an aqueous suspension of a particulate biocompatible material and a biocompatible fluid lubricant. The biomaterial and lubricant are typically combined in a manner that results in a homogenous mixture. It is believed that the lubricant enhances flow in part by preventing particle to particle contact. See, e.g., U.S. Pat. No. 4,803,075. However, a disadvantage of the addition of the lubricant is that can reduce the content of the active component in solution.

Natural polymers or cross-linked biocompatible polysaccharide gels are used in various applications as bio implant material. Highly viscous material is often required, as it is more durable when implanted in the body. However, natural polymers can degrade under heat and light. The cross-linked biocompatible material contains particles and it has been found that it is important to create a set of uniformly sized particles. By properly placing the high intensity light sterilization process and/or an acoustic-wave heat and pressure process in the manufacturing system, it is possible to achieve the highly viscous end product with the benefits of acoustic and/or ultraviolet light sterilization and the benefits of acoustic and/or electrical-wave sizing, without the degradation of the viscosity that conventional methods cause.

Various methods of sterilization are known, including for example, heat sterilization, e.g., autoclaving, irradiation sterilization, e.g., using gamma radiation, and chemical sterilization. Sterilization methods that employ heat and/or pressure require that the process be interrupted and that a sufficient amount of time and energy be employed to bring the material up to temperature and allowed to cool. Sterilization by high-intensity, short-duration pulses of incoherent, polychromatic light in a broad spectrum can be accomplished in a significantly short period of time, within a closed loop system. Most target objects are sterilized or decontaminated within less than a few minutes as only a few flashes, having durations of a few seconds to less than a minute, are required. Sterilization employing high-amplitude ultrasonic sound waves to cause cavitation in a liquid can also be achieved in a short period of time and within the closed loop system. Cavitation occurs when the high-amplitude ultrasonic sound waves create gas-bubble cavities in the liquid. When the cavities collapse they produce intense localized pressures. This cavitation may be induced to destroy liquid-borne organisms, mix fluids or slurries, promote certain chemical reactions and otherwise treat fluids or materials therein.

The cross-linked biocompatible material contains particles, it is important to create a set of uniformly sized particles. The sizing of particles is commonly accomplished by a mechanical means, highly viscous hydrated gels contain particles of various sizes. Uniform sizing is important for the proper function of the bio-compatible material. Sizing can be accomplished within a closed loop system by the use of acoustic or electrical waves.

The process of manufacturing highly viscous hydrated gels comprises: forming an aqueous solution of a water soluble, cross-linkable polysaccharide; initiating a cross-linking agent, and continuing turbulent flow and mixing of the cross-linking agent the material is degassed (air bubbles removed) and then dispensed into various vessels for medical use.

Medical procedures often involve the non-surgical implanting of biomaterials. An example is the injecting of a dermal filler material such as collagen, or the use of highly viscous hydrated gels to suspend particles that carry medication. The particles of a soft tissue augmentation filler typically measure in the range of 150 micron to 800 microns. Uniform particle size is necessary for the proper function of delivery mechanisms such as a syringe. Properly hydrated particles are necessary for the performance of the biomaterial.

The sterilization process of said biomaterial typically involves some form of temperature and/or pressure-based sterilization techniques such as the use of an autoclave. It has been determined that heating and cooling of the autoclave process can change particle size and level of hydration. A properly hydrated particle will not change size after it is implanted in the body. With a properly hydrated particle, injections may be done repeatedly until the desired outcome is affected. This is referred to as 100% correction. An under hydrated particle will pull moisture from surrounding cells after implanting and wills well in size. The welling can cause discomfort so the surgeon must compensate for the under hydrated material by stopping before the desired outcome is affected, this is known as less than 100% correction.

Accordingly, there is a need for an improved flow delivery system for implanting a biomaterial into the human body, where the system does not allow for the needle tip (or cannula and hub assembly) to come disengaged from the leur portion of a syringe. There is also a need for interference with the axial motion of a cannula and hub assembly in the event that sufficient pressure is applied to cause the cannula and hub assembly to become disengaged from the syringe body. Moreover, there is a need for rotatably engaged finger grips for a syringe that are in mechanical engagement with the syringe body. Also, there is a need to provide a container for a cannula and hub assembly that houses the cannula in a sterile environment and covers the sharp end of the cannula while it is not in use as well as a need for providing a tactile and audible response to notify the user that a cannula and hub assembly are properly engaged. Another concern relates to needing a sufficient seal between the leur and hub as well as a seal between the exit orifice of the syringe and entrance orifice of the cannula to eliminate a plenum between the exit orifice of the leur and entrance orifice of the cannula which would otherwise allow unwanted forces to build up at the entrance orifice of the cannula. Additionally, there is a need for a visual cue to allow the user to confirm that the needle is properly engaged. There is also a need for a system that includes a filter that breaks up or downsizes particles of the biomaterial that are larger than desired, to achieve a more effective delivery of the aqueous solution into the body. Finally, there is a need for a process of sterilization of biomaterials without excessive heating and cooling and which facilitates the mixing of a cross-linking agent into a highly viscous hydrated gel as well as improves homogenous sizing of particles within the gel.

The present disclosure addresses these and other needs.

SUMMARY

Briefly and in general terms, the present disclosure is directed towards a flow delivery system which embodies a syringe. In one approach, the syringe includes an outer plastic shell, a leur and a plunger, a needle and/or a catheter having a hub, and a cannula which delivers an aqueous solution of a material. The solution can be a biomaterial or a mixture of biomaterial and a biocompatible fluid lubricant. The cannula and hub assembly can be removably engaged from the distal end of the leur of the syringe and also can be removably engaged with the outer shell or syringe body, in such a manner as to stay engaged when the fluid inside the syringe is placed under sufficient force so as to move dense material through a small diameter cannula.

In another aspect, the present disclosure is directed to a flow delivery system embodying a syringe that includes a cannula and hub assembly which is removably engaged with the distal end of a leur and syringe body. The cannula and hub assembly is first engaged with the distal end of the leur and syringe body in a direction perpendicular to the central axis of the syringe body and secondly in a direction parallel to the central axis of the syringe body, in such a manner as to stay engaged when the fluid inside the syringe is placed under sufficient force so as to move dense material through a small diameter cannula. In the event that sufficient pressure is deployed so as to disengage hub from the syringe body, interference structure is provided so as to prevent the cannula and hub assembly from launching from the distal end of the syringe body.

The present disclosure is also directed towards rotatably engaged finger grips for a syringe that are mechanically engaged with a syringe body that is in turn mechanically engaged with a needle tip. In one specific embodiment, there is provided a cover and container for a cannula and hub assembly engaged with a syringe body in such a manner as to protect and shield the cannula prior to, and after use and provides structure attaching the cannula and hub assembly with the syringe. The disclosure further provides structure that ensures proper engagement by providing an audible or tactile response when the proper engagement between a needle and syringe has been achieved. In one approach, material of appropriate dimension and strength is designed to break-away when sufficient torque has been employed to properly engage the hub with the syringe body. Additional disclosed features allow the user to re-engage the cover with the cannula and hub assembly so as to be able to safely remove the cannula and hub assembly from the syringe body after use and to contain it for proper disposal.

Further, in one preferred embodiment, a cannula and hub assembly are engaged such that there is a seal between the leur and cannula as well as a seal between the hub and leur. To ensure that the needle is properly engaged, a visual indicator can be provided to indicate that the needle has been inserted far enough to ensure proper engagement.

In yet another approach, a filter is located within the body of the syringe. The filter includes a plurality of openings, each of a predetermined size. As the aqueous solution containing the suspended biomaterial particles travels through the body of the syringe under an applied force, the solution encounters the openings in the filter which break up or downsize any particles of the biomaterial within the solution that are larger than the size of the openings. At the same time, the openings in the filter allow any particles of the biomaterial that are smaller than the size of the openings to pass without any downsizing. The size of the openings in the filter may vary and preferably is selected in dependence on the size of the opening or orifice in the needle and/or catheter. The downsized particles then pass together with any other non-downsized particles in a relatively unobstructed manner through the needle and/or catheter and its orifice and into the body.

The filter breaks up any agglomerated biomaterial particle matter or mass into smaller particles of a specific size (i.e., that of the openings in the filter). This reduces the resistance to the flow of the aqueous solution through a flow delivery system that includes the filter, which also reduces the amount of force necessary to transport and expel the aqueous solution through the system and into a body.

The present disclosure is also directed to a manufacturing system which includes the forming of an aqueous solution of a water soluble, cross-linkable polysaccharide; sterilizing the material with one or both of either; high-intensity, short-duration pulses of incoherent, polychromatic light in a broad spectrum, or by the use of high-amplitude ultrasonic sound waves. The process further involves the initiating a cross-linking of said polysaccharide in the presence of a polyfunctional cross-linking agent, and continuing turbulent flow and mixing of the cross-linking agent the material is degassed and then sized before it is dispensed into various vessels for medical use. Natural polymers degrade under heat and light thus decreasing their viscosity. Although decreased viscosity renders the material less durable as a bio-implant, it does render the material more susceptible to homogenous mixing. In the manufacturing process it is often difficult to combine a cross-linking agent in a highly viscous gel. By locating either of the proposed sterilization processes, after the formation of an aqueous solution and before the cross-linking agent is added, the cross-linking agent may be added and thoroughly mixed while the viscosity is low. Acoustic and/or electrical waves may also be employed to create a homogeneous mix of properly sized particles within the highly viscous gel. The viscosity can be regained in the cross linking and de-gassing processes, therefore attaining the benefits of the short-duration sterilization process and retaining the high viscosity of the finished product.

These and other objects, features and advantages of the present invention will become more apparent in light of the following detailed description of preferred embodiments thereof, as illustrated in the accompanying drawings.

BRIEF DESCRIPTION OF THE DRAWING

FIG. 1 including

FIG. 2 including

FIG. 3 including

FIG. 4 including FIGS. 4A-4B, is a detailed section view of the second iteration of the locking tip.

FIG. 5 including FIGS. 5A-5B, is a detailed view of a third iteration of a locking tip.

FIG. 6 including

FIG. 7 including

FIG. 10 including

FIG. 18 including

FIG. 19 including

FIG. 20 including

FIG. 21 including

FIG. 22 including

DETAILED DESCRIPTION

The present disclosure is directed towards a flow delivery system for implanting biomaterial into the human body. The system can include structure prohibiting a needle tip (or cannula and hub assembly) to become disengaged from a leur portion of a syringe. The system can also include structure interfering with the axial motion of a cannula and hub assembly in the event that sufficient pressure is applied to cause the cannula and hub assembly to become disengaged with the syringe body under such force. Rotatably engaged finger grips for a syringe that are in mechanical engagement with the syringe body are also disclosed as is a container for a cannula and hub assembly that contains the cannula in a sterile environment and covers the sharp end of the cannula while it is not in use. In one approach, the system can include a tactile and audible response to notify the user that a cannula and hub assembly are properly engaged. Moreover, there is disclosed a seal between the leur and hub as well as a seal between the exit orifice of the syringe and entrance orifice of the cannula to eliminate a plenum between the exit orifice of the leur and entrance orifice of the cannula. Additionally, where desirable, there is provided a visual cue to allow the user to confirm that the needle is properly engaged as well as a system that includes a filter that breaks up or downsizes particles of the biomaterial.

Figures 1A, 1B:
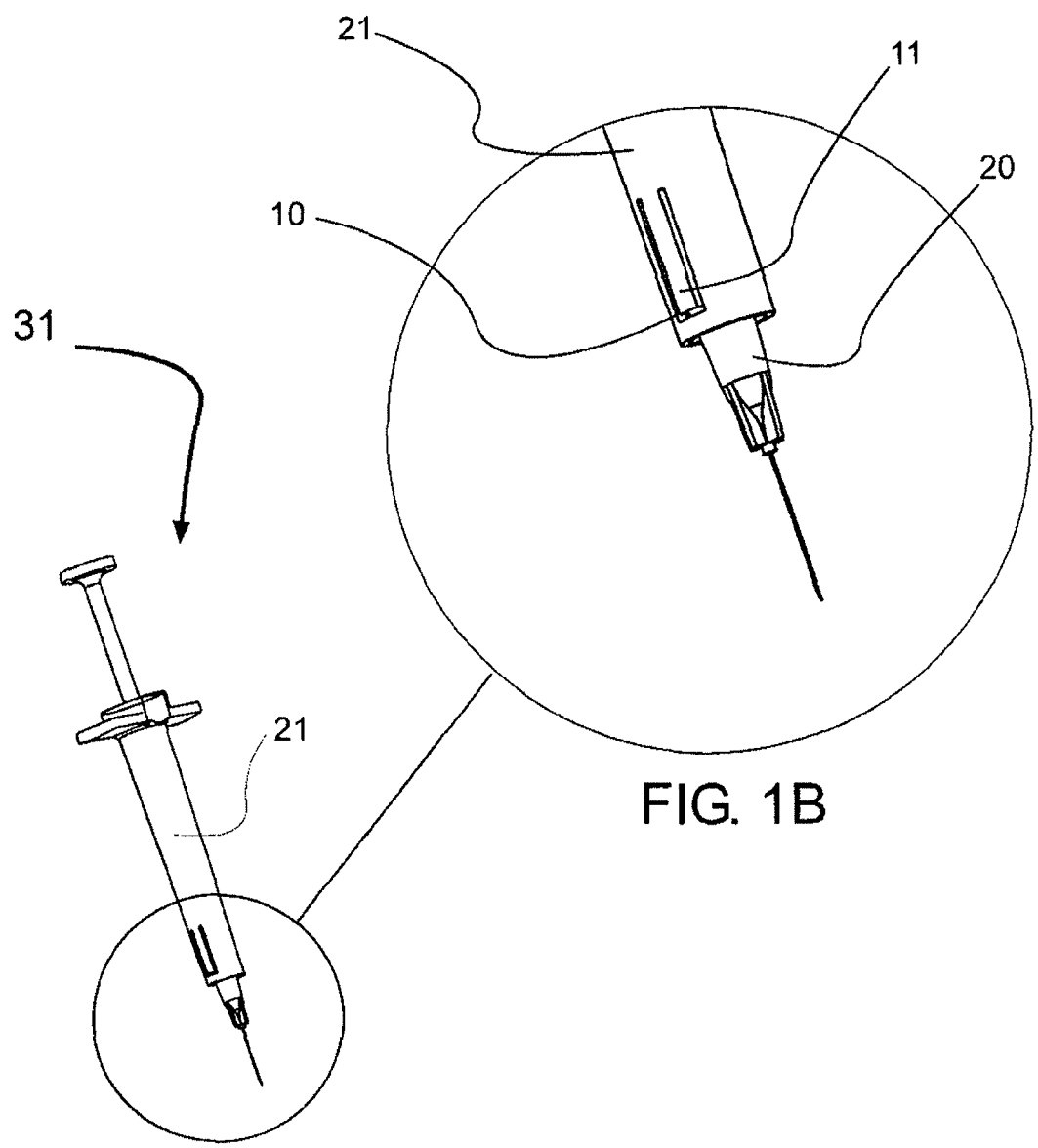
FIGS. 1A-1B, is a perspective and detailed view of a first iteration of a locking tip for a syringe.
Figures 2A, 2B:
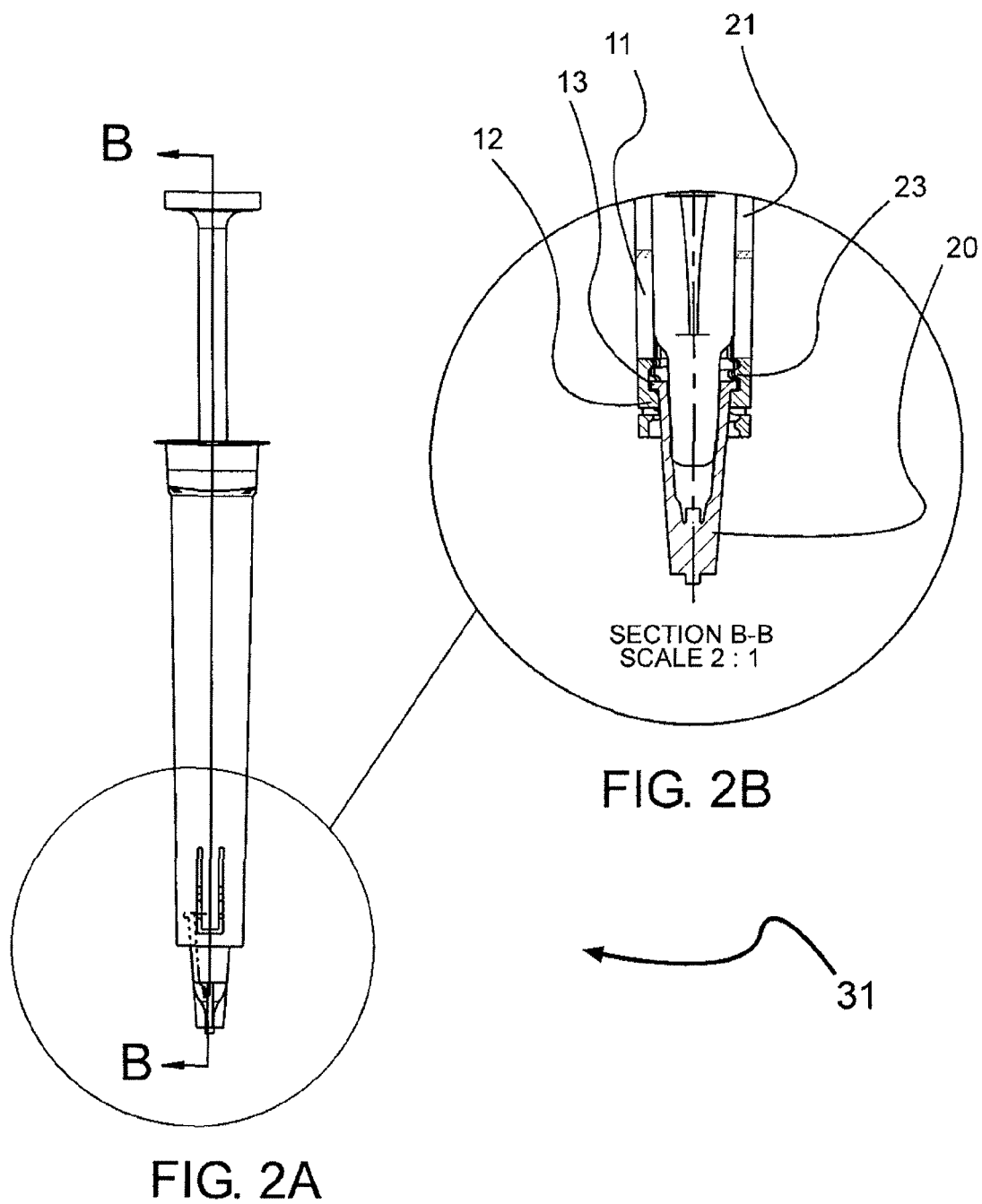
FIGS. 2A-2B, is a detail section view of the first iteration of the locking tip.
Figures 3A, 3B:
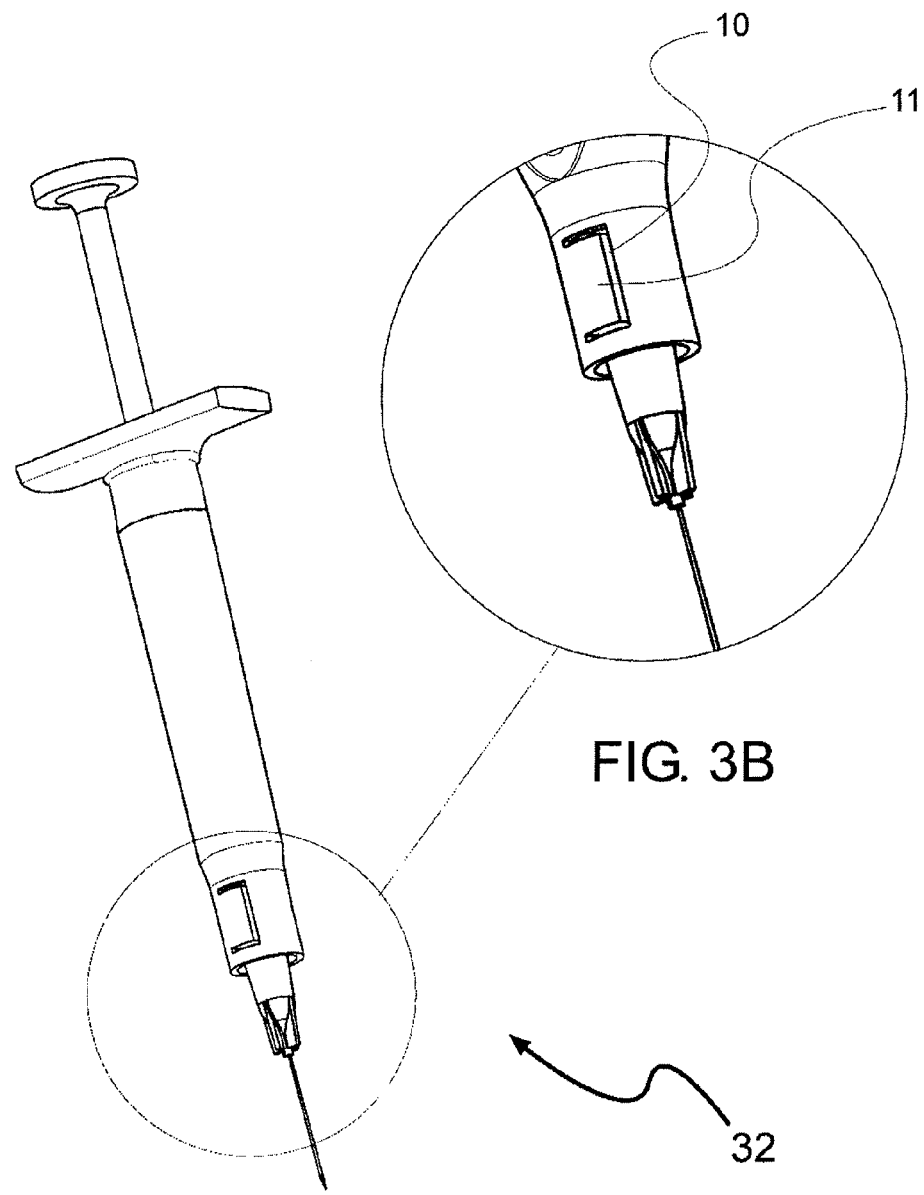
FIGS. 3A-3B, is a detailed view of a second iteration of a locking tip.

In the figures, like reference numerals refer to like elements. Referring to FIGS. 1A and 1B, in a first iteration of a syringe assembly 31, a feature is added to a syringe body 21 that provides a locking mechanism that prevents the cannula and hub assembly 20 from dislodging or becoming disengaged from the syringe body 21. The feature is embodied in a cut 10 in the surface of the syringe body 21 that creates a flexible portion 11 that has a protrusion 12 (See FIG. 2, FIG. 2B). A cross section of the first iteration is shown in FIGS. 2A and 2B. The cannula and hub assembly 20 is engaged with the syringe body 21 by threads 23. Clockwise motion of the hub 20 into threads 23 engages the cannula and hub assembly 20 with syringe body 21. In the previous approaches, counter-clockwise motion of the cannula and hub assembly 20 in threads 23 disengages the cannula and hub assembly 20. The protrusion 12 is ramp-shaped, as the ridge 13 is engaged in a clockwise direction through the threads 23, the flexible portion 11 flexes outward as the ridge 13 moves along the ramp portion of the protrusion 12. As the ridge drops off the high end of the ramp, the flexible portion 11 flexes back to a normal position in which the protrusion 12 interferes with the passage in a counterclockwise direction of the ridge 13 and thus retains the cannula and hub assembly 20 engaged with the syringe body 21.

The second iteration of the syringe assembly 32 is illustrated in FIGS. 3A, 3B, 4A and 4B. In the second iteration of the syringe assembly 32, a similar system to the first iteration is proposed in which the cut 10 and flexible portion 11 function in a similar manner to the first iteration except that there is a 90 degree alteration in the orientation of the feature. The protrusion 26 also functions in a similar manner so as to interfere with the passage in a counterclockwise direction of the ridge 13.

The third iteration of the syringe assembly, 33 is illustrated in FIGS. 5A and 5B. A series of ramp shaped protrusions 24 are positioned along threads 23 in the syringe body 21. The ramp shaped protrusions 24 cause a decrease in the inside diameter of the syringe body and therefore increased pressure on the ridge 13. As the ridge 13 on the cannula and hub assembly 20 is engaged in a clockwise direction with the threads 23 on the syringe body 21, the ridge 13 meets gradually increasing interference from the ramp-shaped protrusions 24 followed by a decrease in interference after dropping of the high end of the ramp. The high end of the ramp-shaped protrusions 24 prevent counterclockwise movement of the ridge 13. The interference caused by the ramp shape protrusions 24 prevent the cannula and hub assembly 20 from moving in a counterclockwise direction after having been engaged with the syringe body 21 in a clockwise direction.

Figures 6A, 6B:
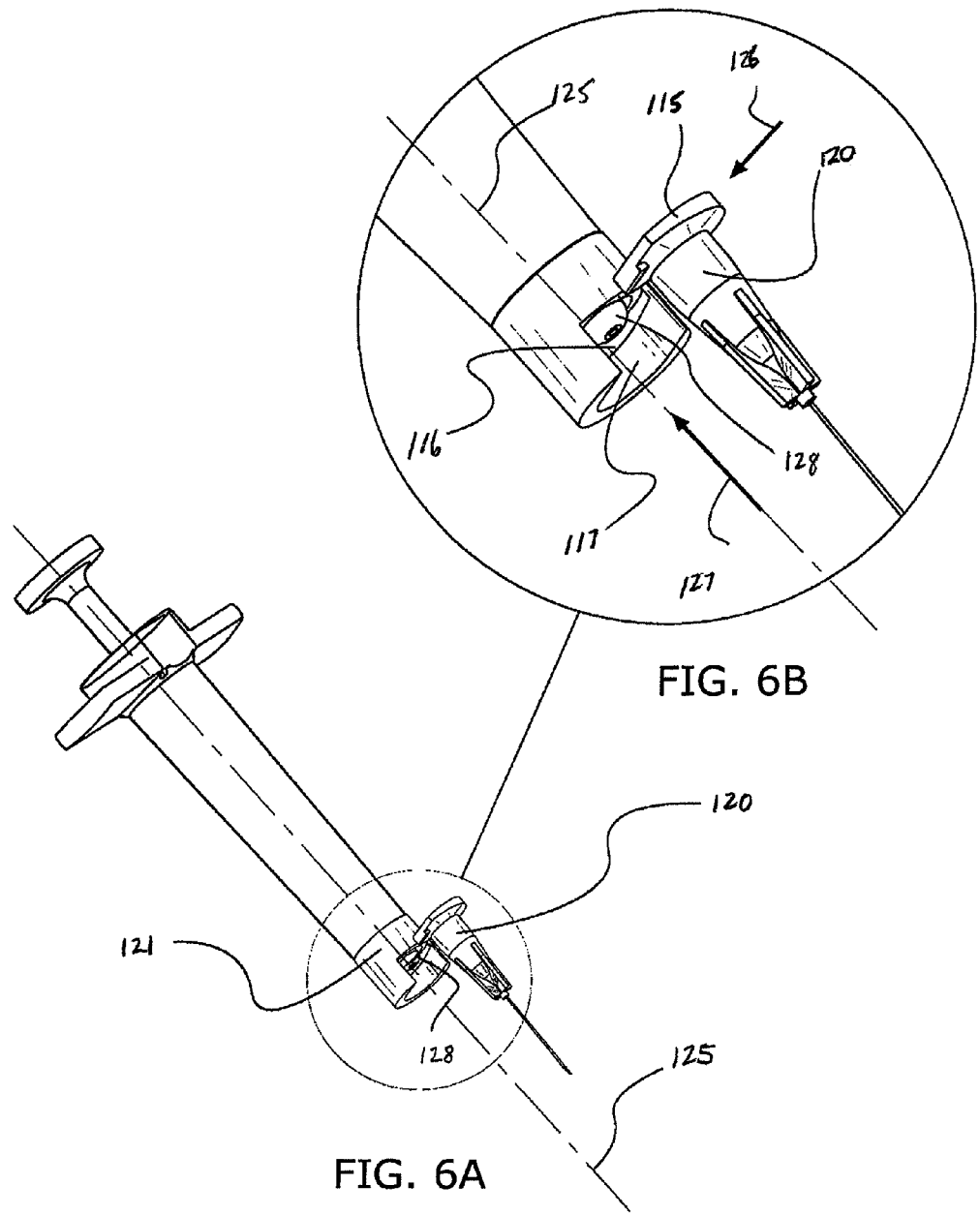
FIGS. 6A-6B, is a detailed view of a syringe with a lateral lock.
Figures 7A, 7B:
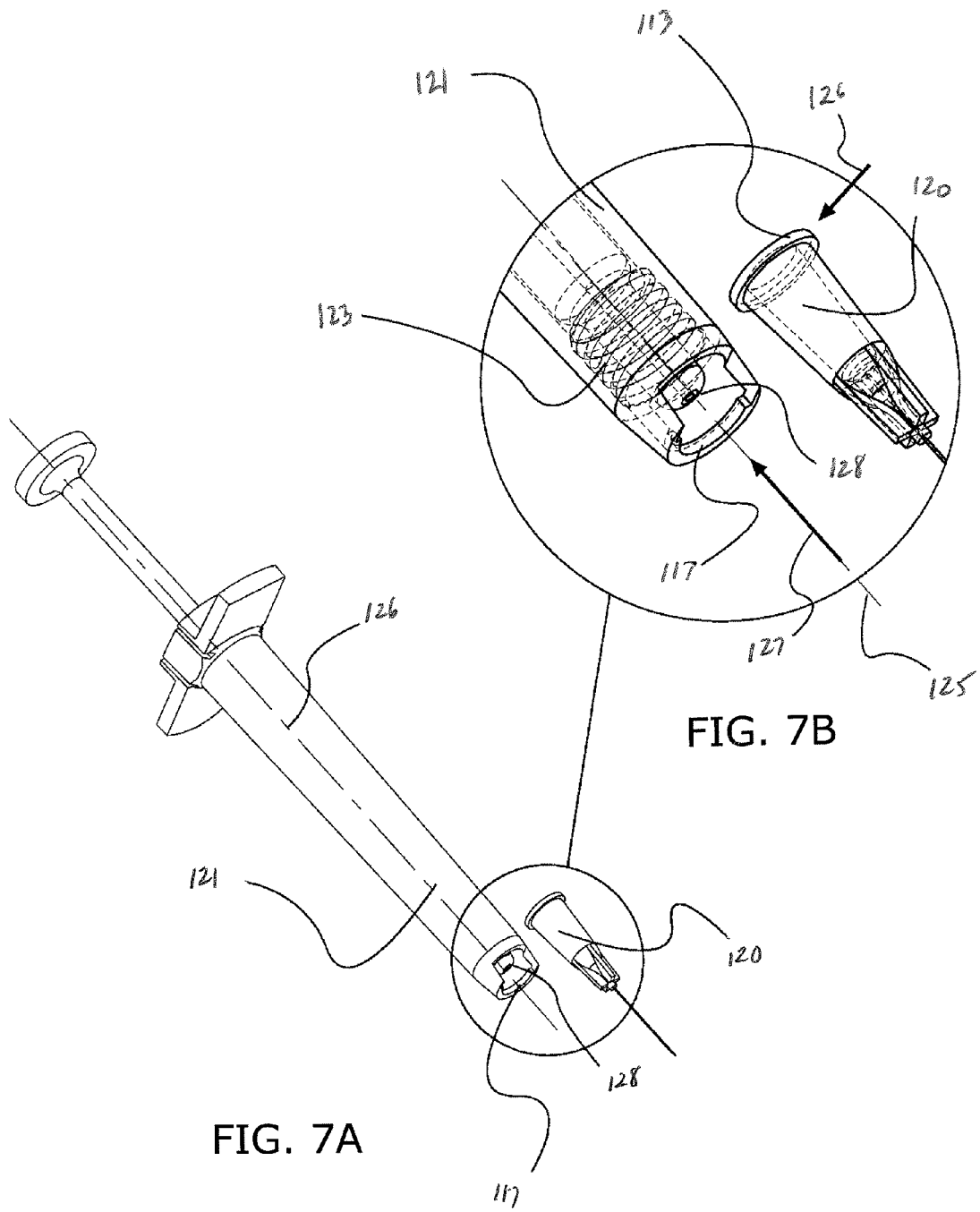
FIGS. 7A-7B, is a detailed view of a second iteration of a lateral lock.

Other features of the contemplated syringe assembly is presented in FIGS. 6 and 7 including 6A, 6B, 7A and 7B. The syringe assembly includes an outer housing, a cannula and hub assembly 120 and a leur. The outer housing has a central axis 125. The syringe assembly includes structure which, in combination the cannula and hub assembly 120 and the syringe body 121 are engaged in first a lateral direction 126, perpendicular to the central axis 125 of the syringe assembly and then in an axial direction 127, parallel to the central axis 125 of the syringe body (See FIGS. 6A, 6B). The cannula and hub assembly 120 has a rotatably tapered ridge 115 that engages with a similarly tapered slot 116 after it is moved laterally into position. The tapered ridge 115 moves along the similarly tapered slot 116 in such a manner as to move the cannula hub assembly 120 along the central axis 125 in a direction 127 so as to create a seal between the hub assembly 120 and the leur 124. The cannula and hub assembly 120 has a conical shape that meets the conical shape of the distal end 128 of the leur so as to create a liquid tight seal. Such a seal as is created by two conical sections meeting, is a common method of creating a liquid tight seal.

In the second iteration of the contemplated syringe assembly (FIGS. 7A and 7B), threads 123 engage with ridge 115. The cannula and hub assembly 120 engages in a direction 126 perpendicular to the central axis 125 of the syringe body, at which point the threads 123 engage with the ridge 15. By rotating the cannula and hub assembly 120 in a clockwise direction, the cannula and hub assembly 120 moves in a direction 127 parallel to the central axis 125 of the syringe body 121. Movement of the cannula and hub assembly 120 in the direction 127, engages the conical shape of the cannula and hub assembly 120 with the distal end 128 of the leur 124, thus creating a liquid tight seal. The assembly further includes a smaller opening 117 (FIG. 6, FIG. 7) at the distal end of the syringe body that provides interference with the ridge on the hub 115, in the event that the cannula and hub assembly 120 become disengaged from the syringe body and leur. The open end 117 of the syringe body 121 is too small for the ridge 115 to pass. Under considerable pressure, the cannula and hub assembly 120 may be forced in such a manner as to come disengaged with the syringe 121, however, motion in the axial direction will be stopped by the smaller opening 117 thus preventing the cannula and hub assembly from being launched from the distal end of the syringe assembly.

Figure 8:
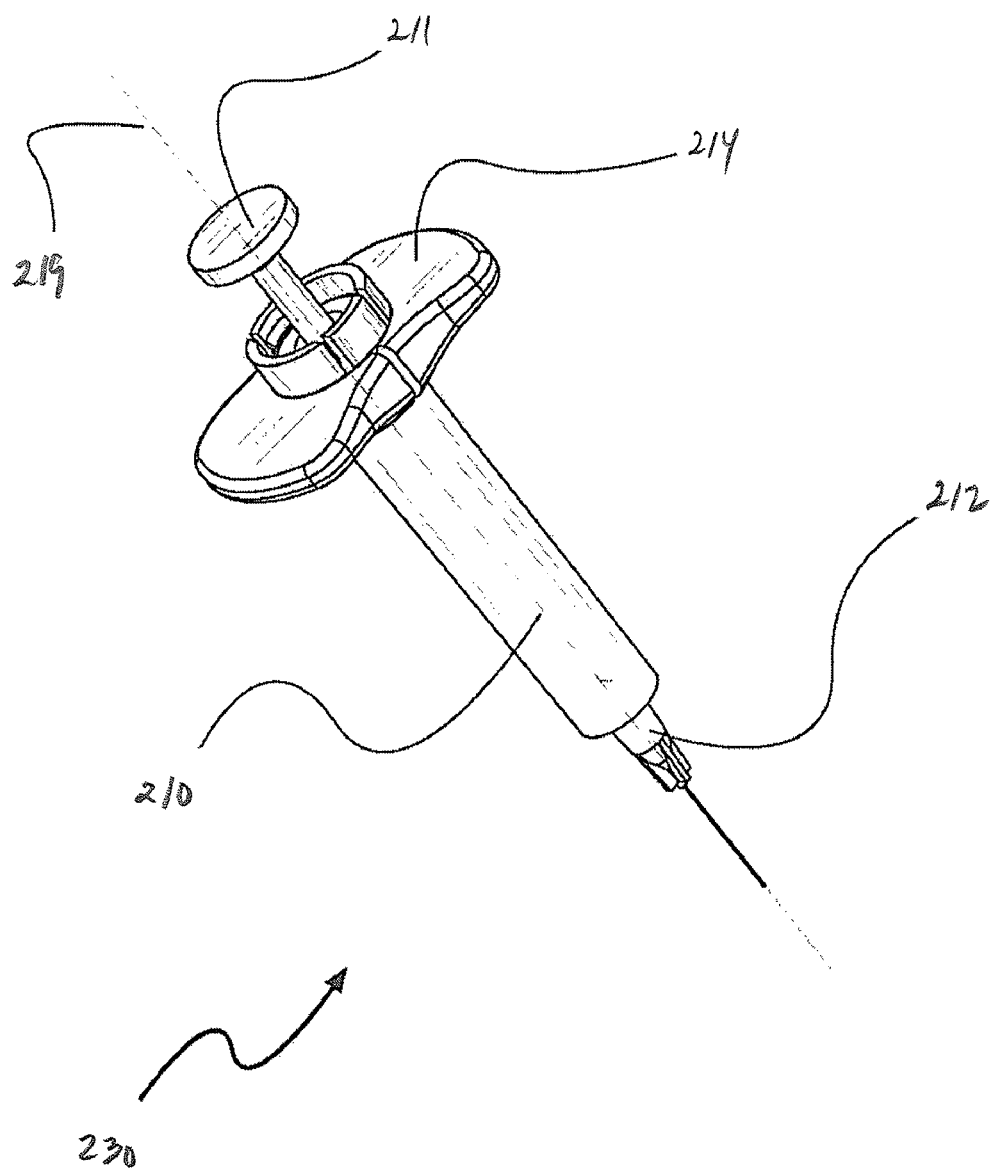
FIG. 8 is a perspective view of a syringe with a rotating finger grip.
Figure 9:
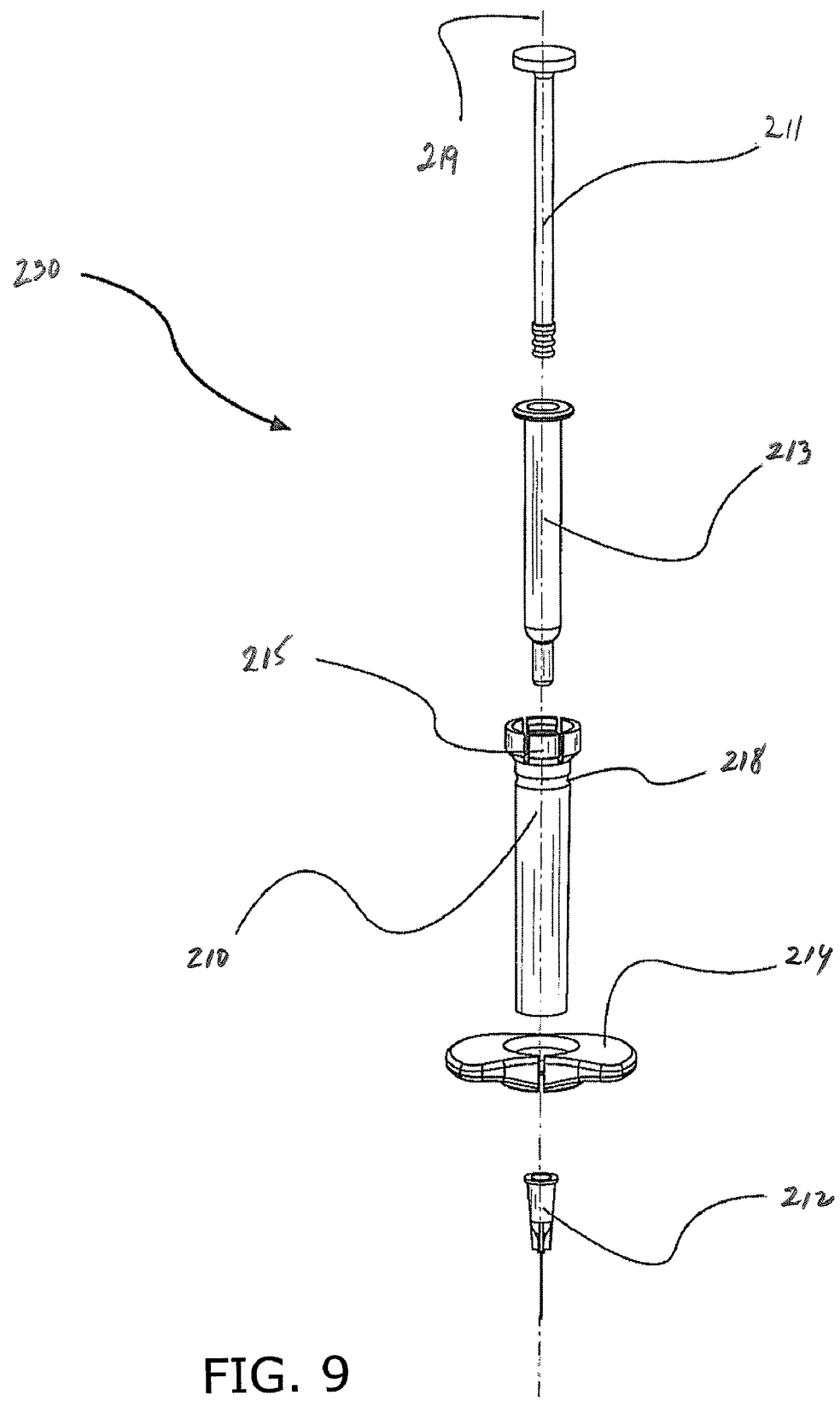
FIG. 9 is an exploded view of the assembly of FIG. 8.
Figure 10A:
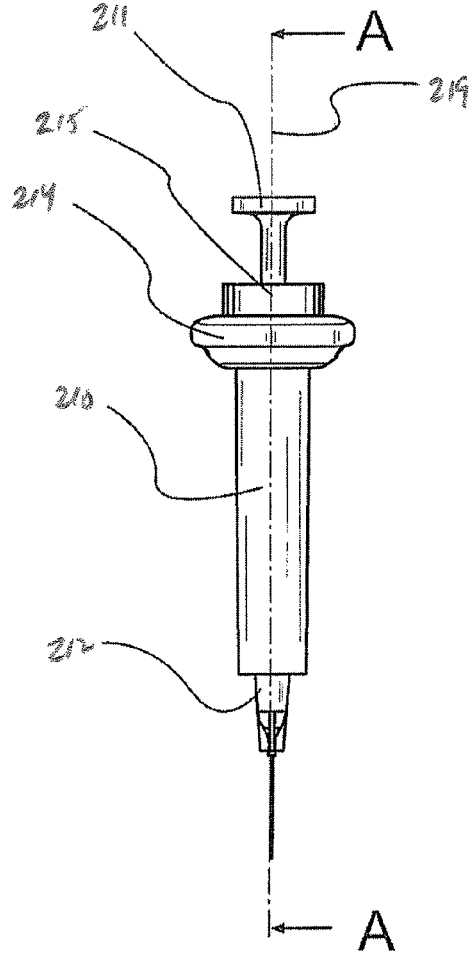
FIGS. 10A-10B is a section view of the assembly of FIG. 8.
Figure 10B:
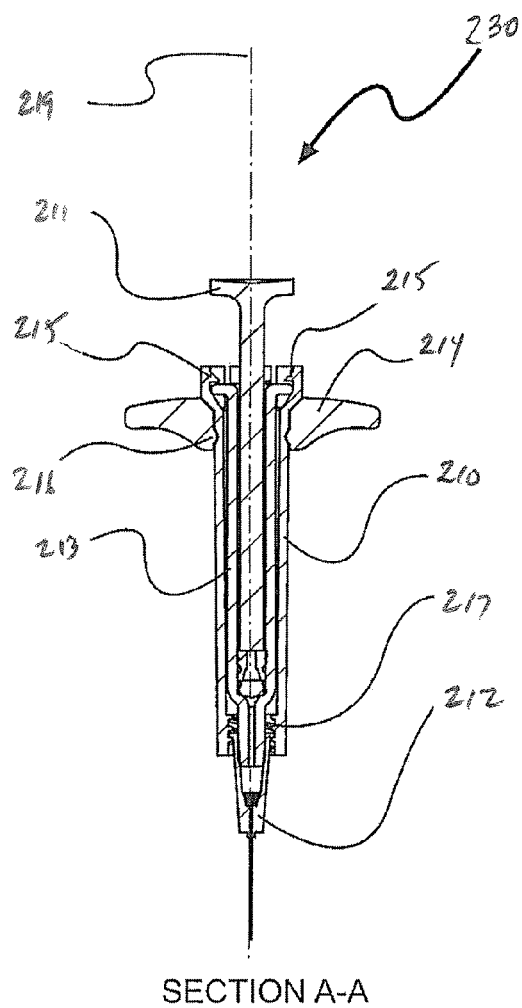
Figure 11:
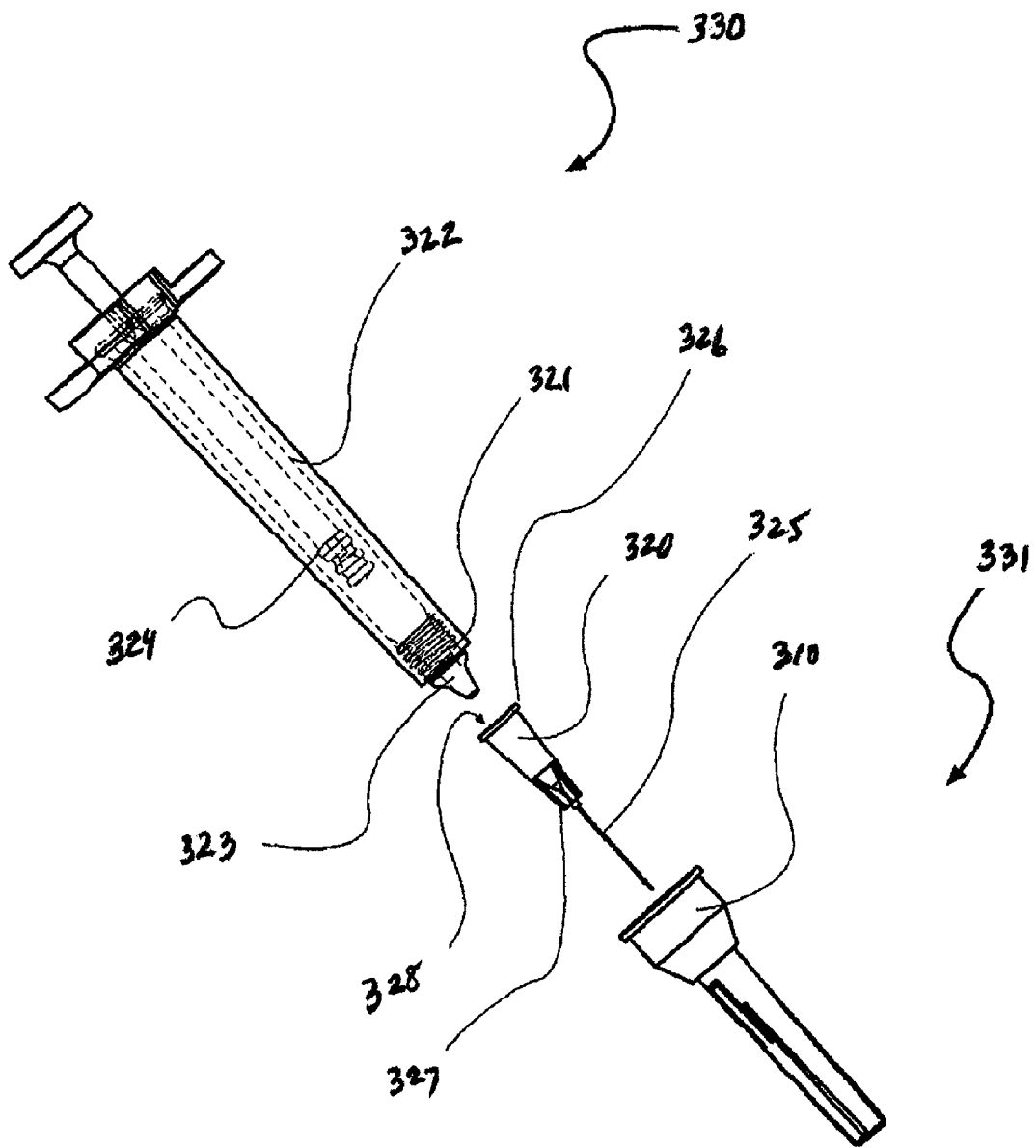
FIG. 11 is a perspective, exploded view of a torque sensitive cannula engaged with a syringe

Turning now to FIG. 8 through FIG. 10, a syringe assembly with a central axis 219 includes an outer shell (or syringe body) 210 with an interior leur 213 and a plunger 211 that is moveably engaged with the leur 213. The syringe body has a proximal and distal end and is wider at the proximal end and narrower at the distal end. The proximal end of the needle 212 is removably engaged with the distal end of the leur 213 and the syringe body 210. The needle is engaged with the syringe body by threads 217 in such a manner that when the needle is rotated it moves upward along the syringe body 210 and firmly engages with the distal end of the leur 213.

The leur 211 is engaged with the syringe body 210 along the central axis 219 and fits inside the syringe body 210. Protrusions 215 flex outward as the leur is positioned and snap into place to hold the leur 211 in the syringe body 210. Finger grips 214 embody a form that is engaged along the central axis 219 of the syringe body. The finger grips are engaged from the distal end of the syringe and moved toward the proximal end of the syringe body 210 and are engaged with the larger proximal end of the syringe body 210 in such a manner as not to allow the finger grips to slide off of the proximal end of the syringe body. A protrusion 216 on the finger grips 14 is engaged with a detent 218 (FIG. 9) on the syringe body 210. The protrusions 216 and detent 218 prevent the finger grips from sliding downward along the syringe body 210.

The finger grips 214 are rotatably engaged with the syringe body 210. Notably, the syringe body 210 is in direct mechanical engagement with both the finger grips 214 and the needle 212 in such a manner that allows rotation of the finger grips 214.

In the embodiments of the present invention described above, it will be recognized that individual elements and/or features thereof are not necessarily limited to a particular embodiment but, where applicable, are interchangeable and can be used in any selected embodiment even though such may not be specifically shown.

Figure 12:
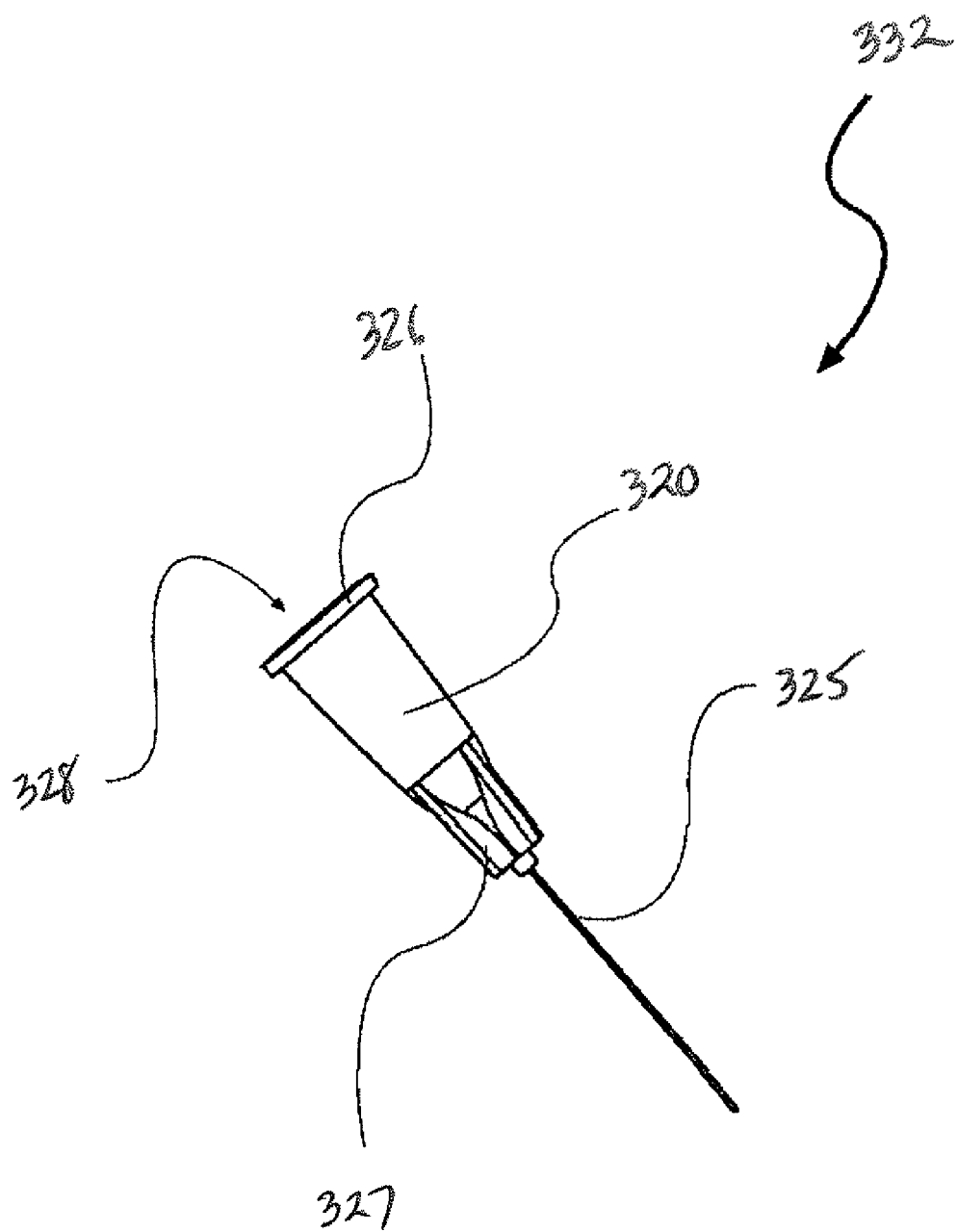
FIG. 12 is a perspective view of the cannula and hub assembly of FIG. 11.
Figure 13:
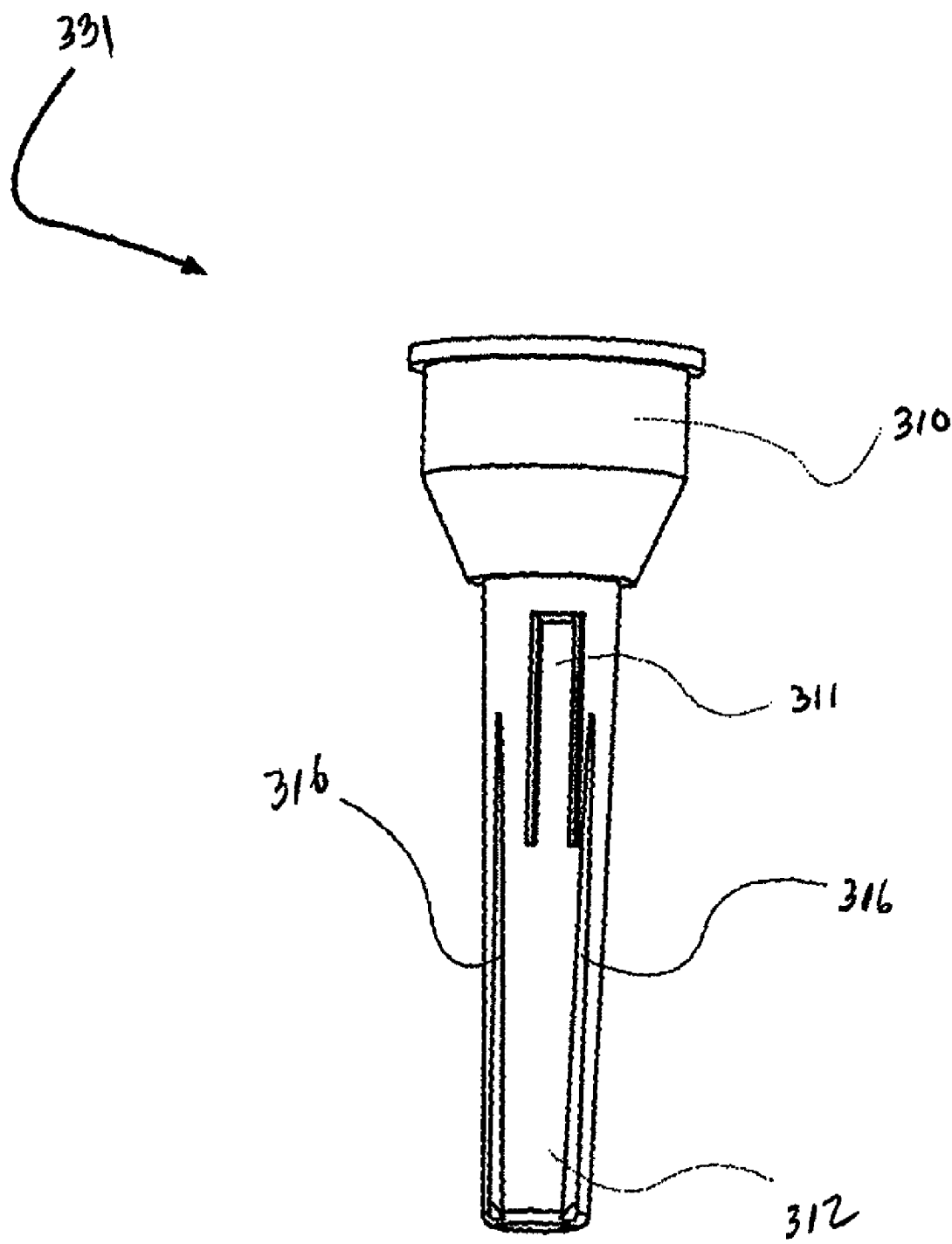
FIG. 13 is a perspective view of the cannula.
Figure 14:
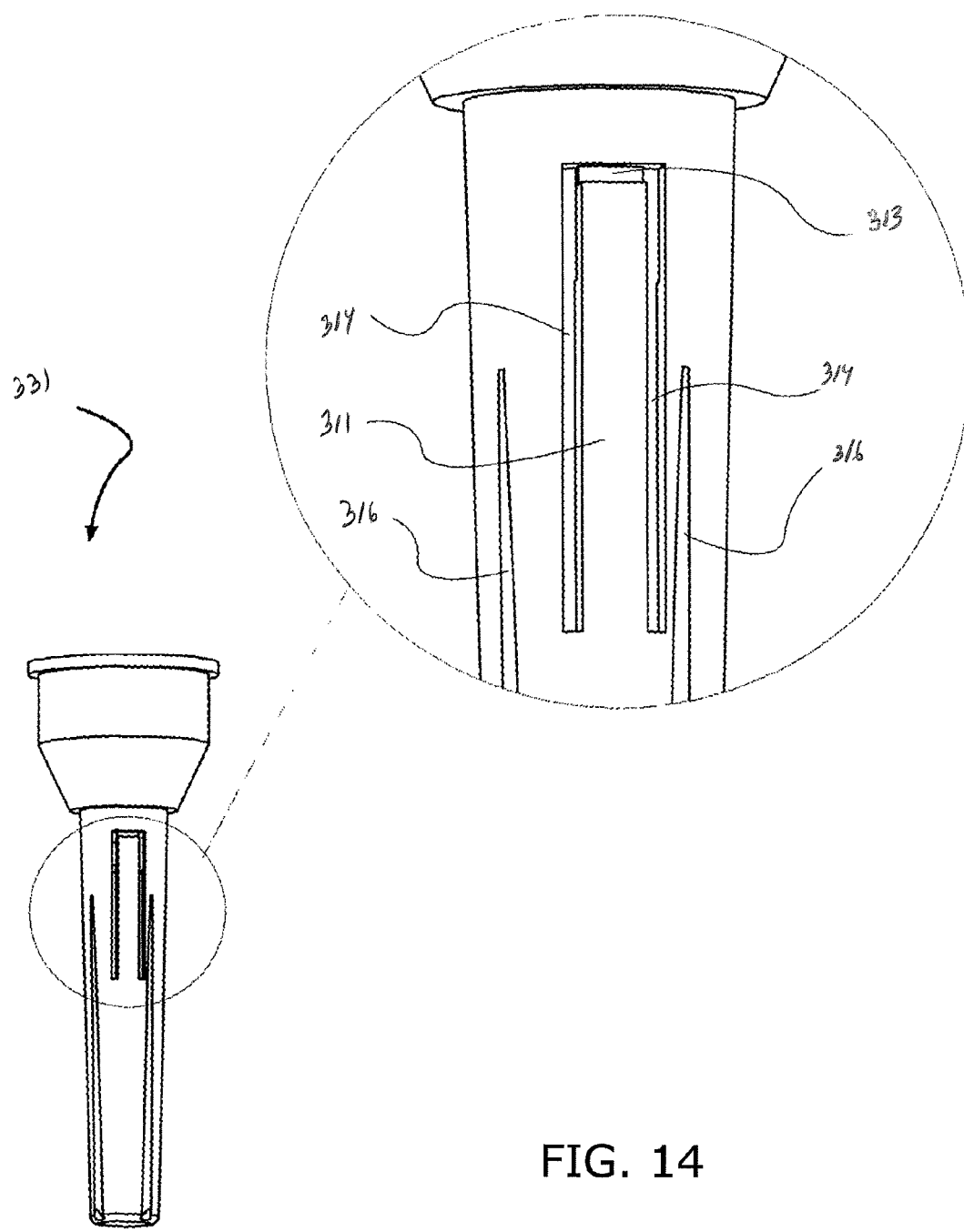
FIG. 14 is a detail view of the cannula of FIG. 11.

Referring to FIG. 11 through FIG. 16, a single use syringe with a removable tip is described. The syringe assembly embodies an outer shell 322 with an interior leur 323 and a plunger 324 that is moveably engaged with the leur 323. The needle is comprised of a cannula 325 engaged with a hub 320. The cannula 325 and hub 320 are permanently engaged and make up the cannula and hub assembly 332 (FIG. 12). The hub 320 (FIG. 11) is removably engaged with the leur 323 and the outer plastic shell 322. The interior surface of the hub 28 is engaged with the distal end of the leur 323. The outer surface of the hub is flared at the top 326 to engage with threads 321 in the outer shell 322. As the flange 326 on the hub 320 is engaged with the threads 321 of the outer shell 322 it moves upward and thus engages the interior surface of the hub 328 with the distal end of the leur 323. The conical shape of the hub 20 provides a seal with the distal end of the leur 323 when sufficient torque is exerted on the hub 320 to properly thread the flared ridge 326 into the threads 321 of the syringe body 322. The cannula and hub assembly 332 is stored in the cap 331. The cap 331 provides a sterile container for the cannula and hub assembly 332 and also protects the user from being pricked by the cannula 325 while assembling the syringe 330.

To assemble the syringe the user inserts the cannula and hub assembly 332 into the syringe 330, the cannula and hub assembly 332 is left inside the cap 331 while threading the ridge 326 of the hub 320 into the threads 321 of the syringe body 322. Ribs 316 (FIG. 13) along the longitudinal axis of the container 310 provide a grip for the user's finger tips. Fin-like protrusions 327 on the hub 320 engage with the rectangular shaped portion 312 of the container 310, thus not permitting the hub 320 to rotate inside the cap 331. When the hub 320 is sufficiently engaged with both the syringe body 322 and the distal end of the leur 323 the cap 331 is removed and the syringe is ready for use. If the cannula and hub assembly 332 is not sufficiently engaged with the syringe body 322, it can become disengaged during use and, when under sufficient pressure, can become a sharp projectile.

Figure 15:
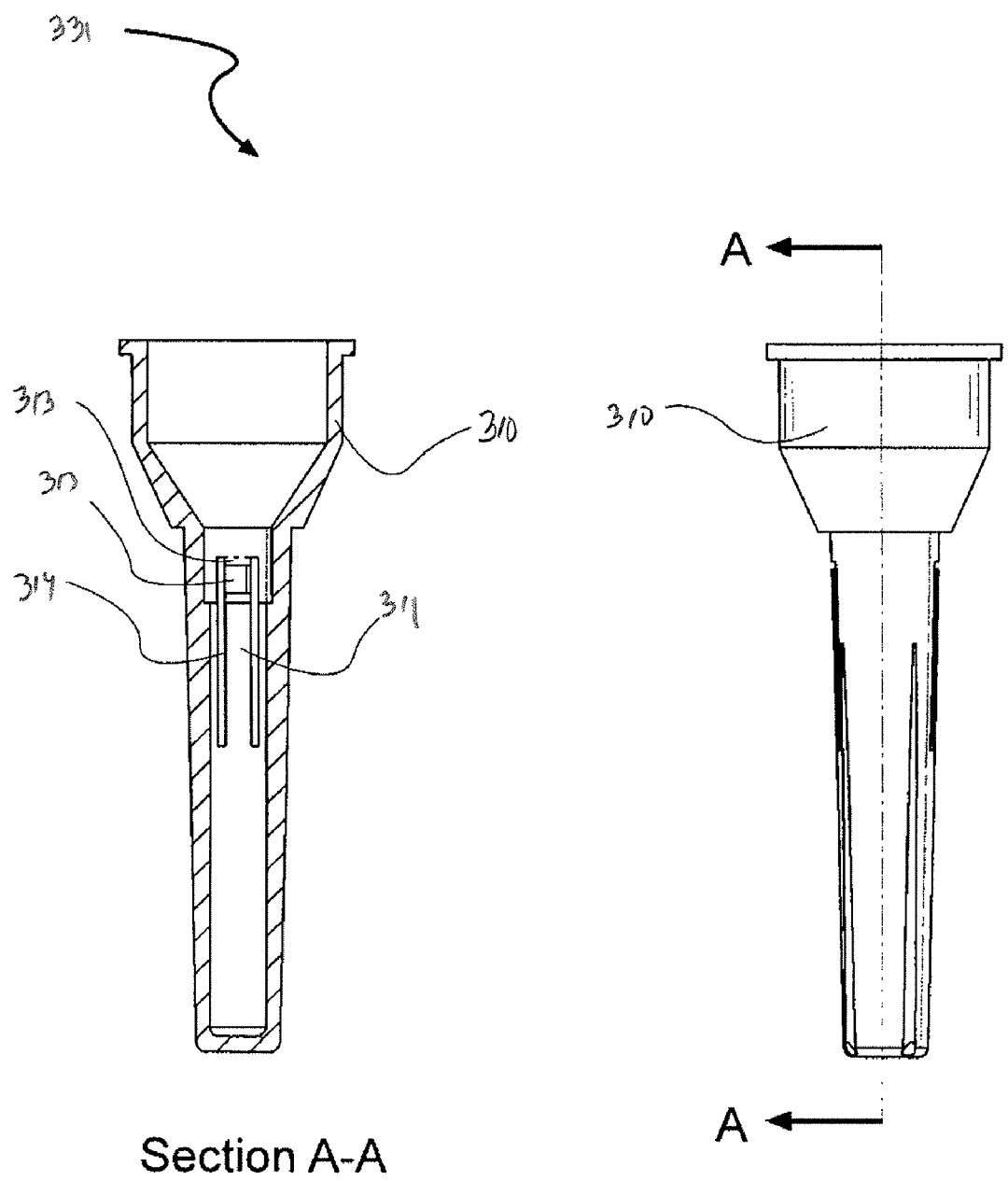
FIG. 15 is a section view of the cannula of FIG. 14.
Figure 16:
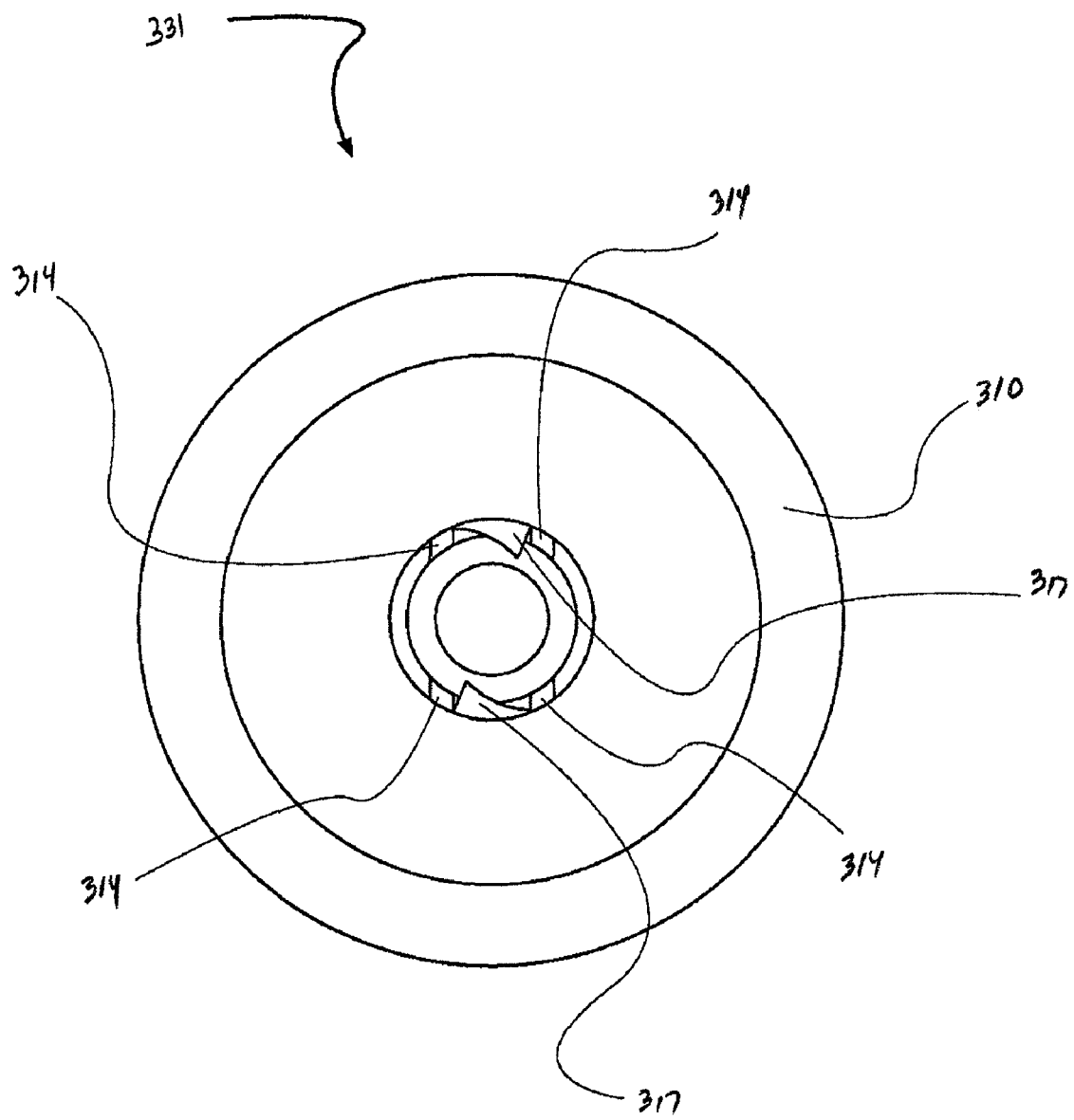
FIG. 16 is a top view of the cannula of FIG. 15.
Figure 17:
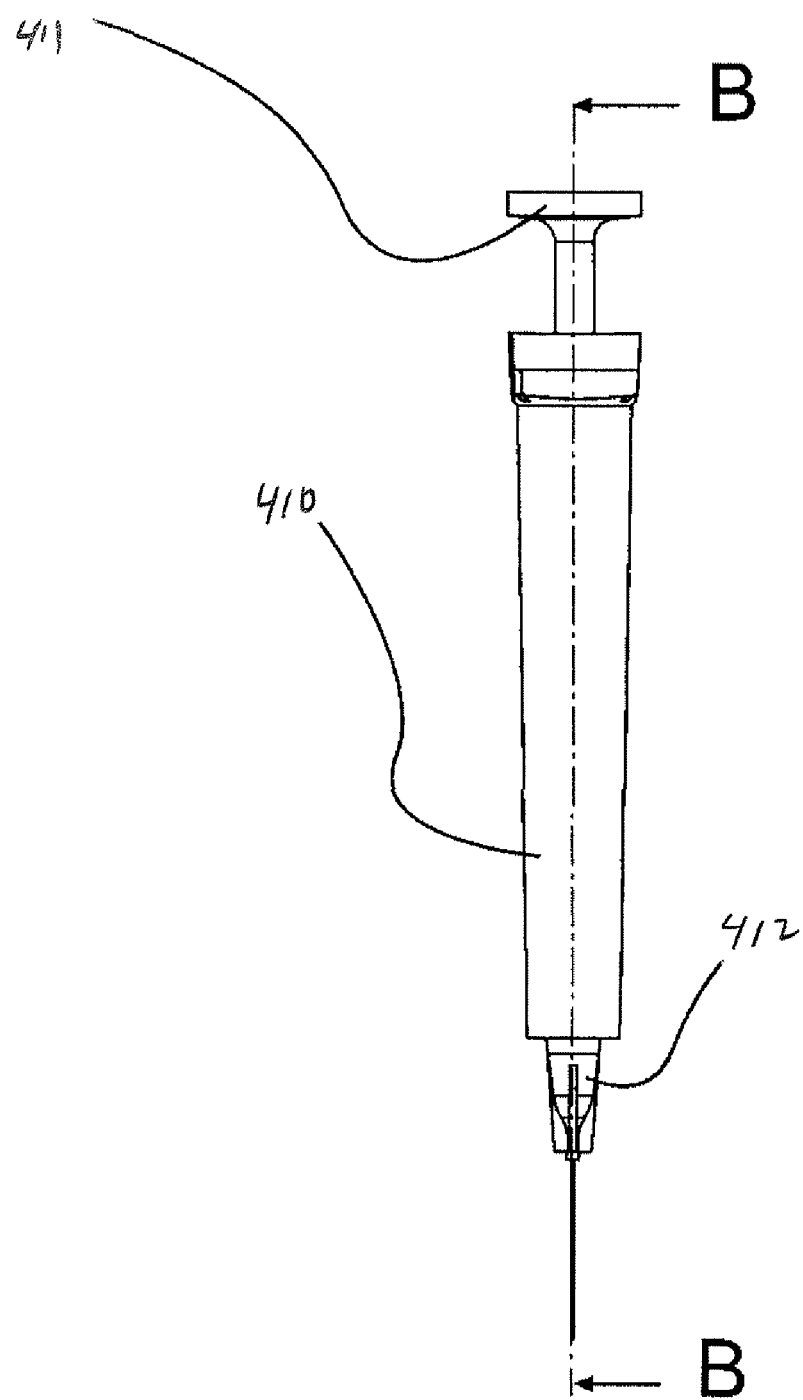
FIG. 17 is a side view of another embodiment of a syringe assembly.

The present structure provides a tactile and/or an audible response to alert the user that the hub 320 is properly engaged with the syringe body 322 and the distal end of the leur 323. The syringe assembly includes a body portion 310 that houses the cannula and hub assembly 332, and further comprises ridges 316 along the longitudinal axis of the body 310, protrusions 317, a cut 314 in the surface of the body 310, a partial cut 313 and a flexible portion 311 (FIGS. 13-16). When the cannula and hub assembly 332 is engaged with the cap 331 the protrusions 17 (FIG. 16), engage with the fin-like protrusions 327 on the hub 320. The protrusion 317 are formed as part of the flexible portion 311, within the boundary created by the cuts 314 and the partial cut 313 are located on the inner surface of the flexible portion 311 (FIGS. 15, 16). The partial cut 313 is configured so as to break through when a specified amount of torque is applied to the cap 331 as the fin-like protrusion 327 bear against the protrusion 317. When the partial 313 breaks, an audible response is provided. The protrusion 317 are attached to the flexible portion 311 and thus will flex outward as they engage with the fin-like protrusion 327. When the protrusion 317 flex outward, there is no longer enough interference with the fin-like protrusion 327 to continue rotating the cannula and hub assembly 332. Furthermore, as the flexible portions 311 flex outward, they press against the user's fingertips, providing a tactile response. When the user wishes to remove the cannula and hub assembly 332 from the syringe body 322, the flexible portion 311 may be depressed, thus engaging the protrusions 317 with the fin-like protrusion 327 so as to provide sufficient grip to remove the cannula and hub assembly from syringe body.

Again, in the embodiments of the present invention described above, it will be recognized that individual elements and/or features thereof are not necessarily limited to a particular embodiment but, where applicable, are interchangeable and can be used in any selected embodiment even through such may not be specifically shown.

Figures 18A, 18B:
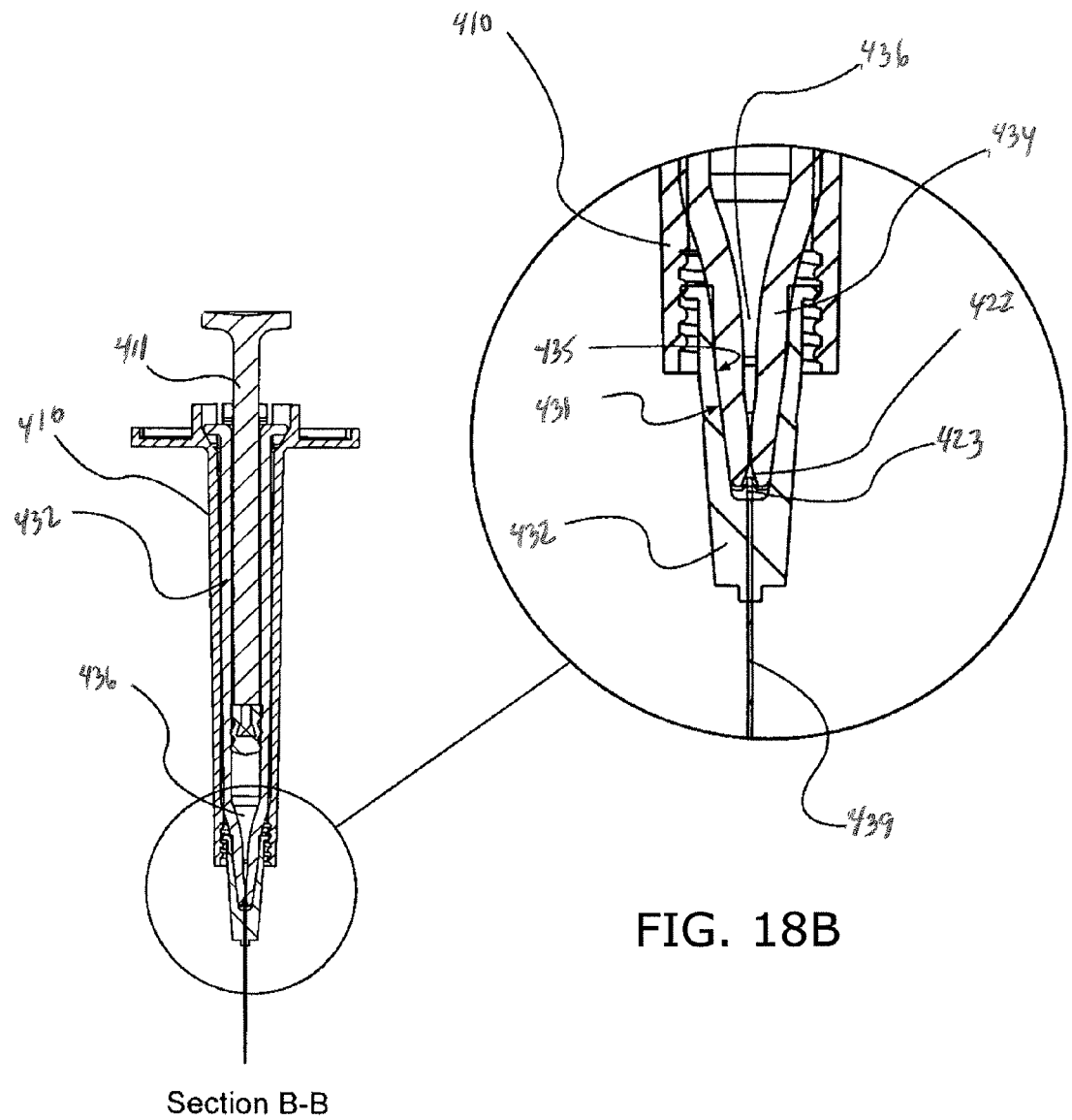
FIGS. 18A-FIG. 18B, is an enlarged section view of the interface structure of the syringe assembly of FIG. 17.

In yet another approach, an useful interface between the cannula and leur as well as an interface between the leur and hub is provided. Here the syringe assembly embodies an outer shell 410 and plunger 411, with a unique leur 434 that has a contoured outer surface at its distal end 435 (FIG. 18). A hub 432 has a contoured inner surface 431. A cannula 439 has a contoured proximal end 423 that engages with a contoured distal end 422 of the leur 434. The interior surface of the leur comprises a gradual taper 436 that, at the small end of the taper, approaches the diameter of the cannula 423. The hub 432 has an inner surface 431 that is contoured to fit the end 435 of the leur 434. The proximal end of the cannula 423 is tapered so as to fit into, and create a tight seal with the tapered distal tip 422 of the leur 432. The tight seal between the proximal end of the cannula and the leur 435, eliminates an undesirable plenum 420. The material inside the leur is forced through the gradually tapered contour 436. Pressure created by the force of the plunger along the interior of the leur 434 is exerted against the inner walls of the leur and does not build up in a manner that has the potential to dislodge the hub 432 from the end 435 of the leur 434.

Figures 19A, 19B:
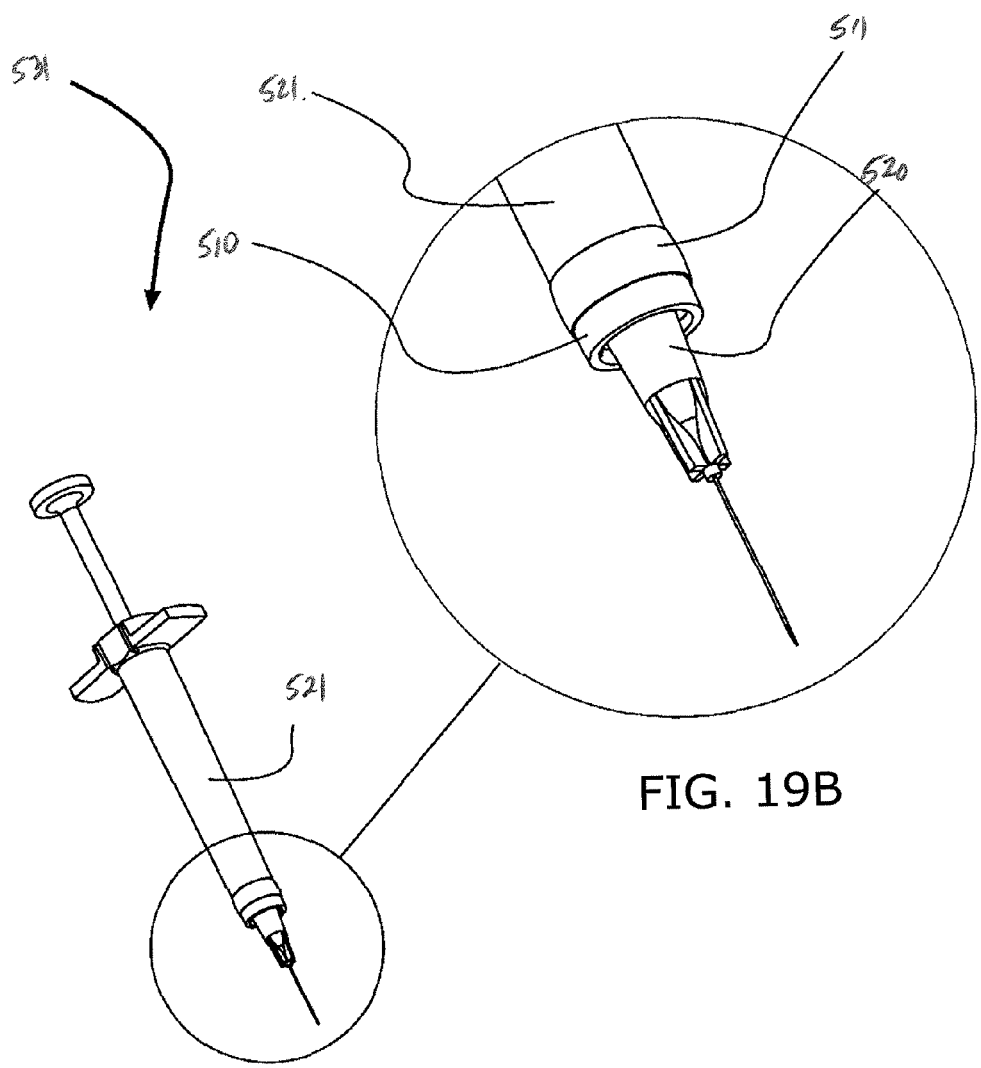
FIGS. 19A-19B, is a perspective and detailed view of one approach to a visual indicator.
Figures 20A, 20B:
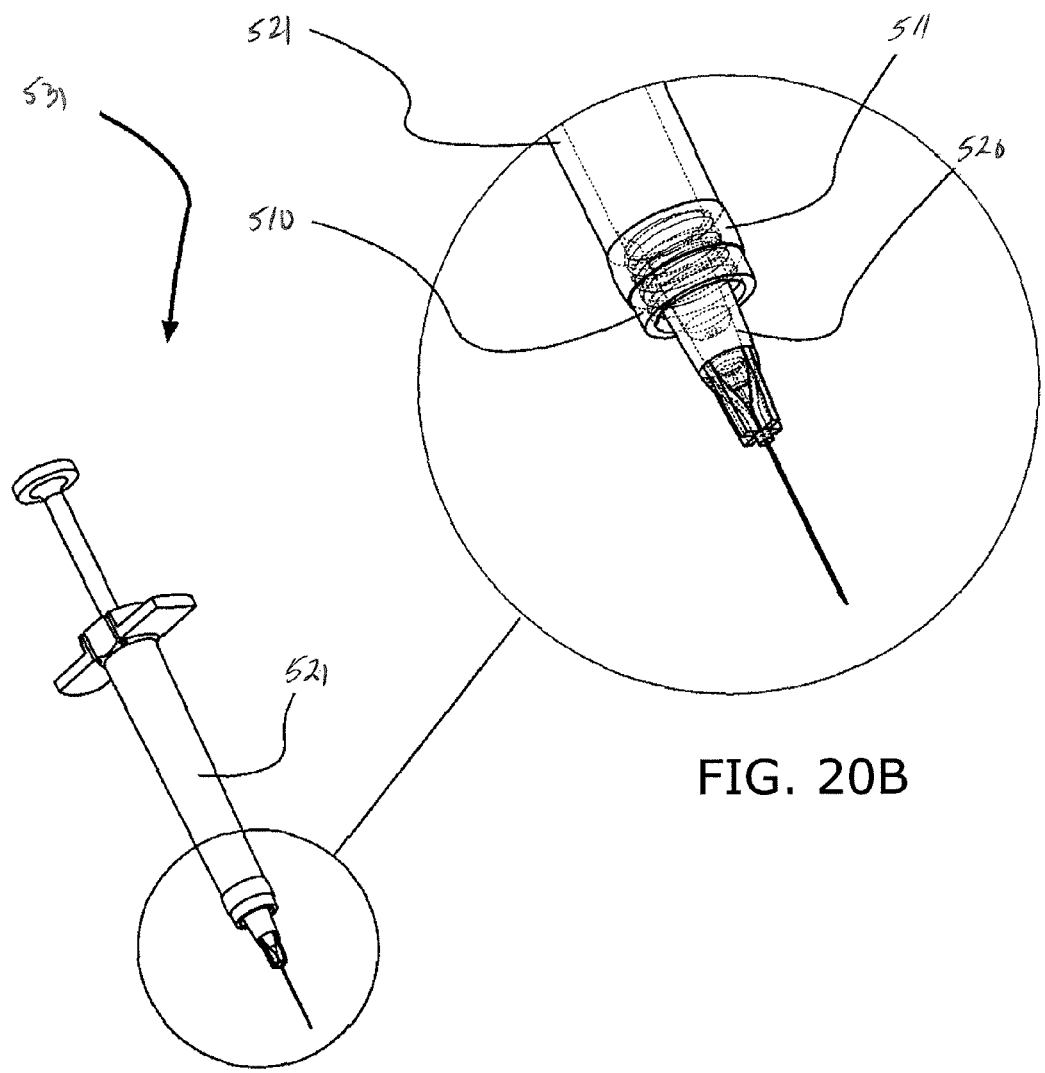
FIGS. 20A-20B, is a detail view of the visual indicator.
Figures 21A, 21B:
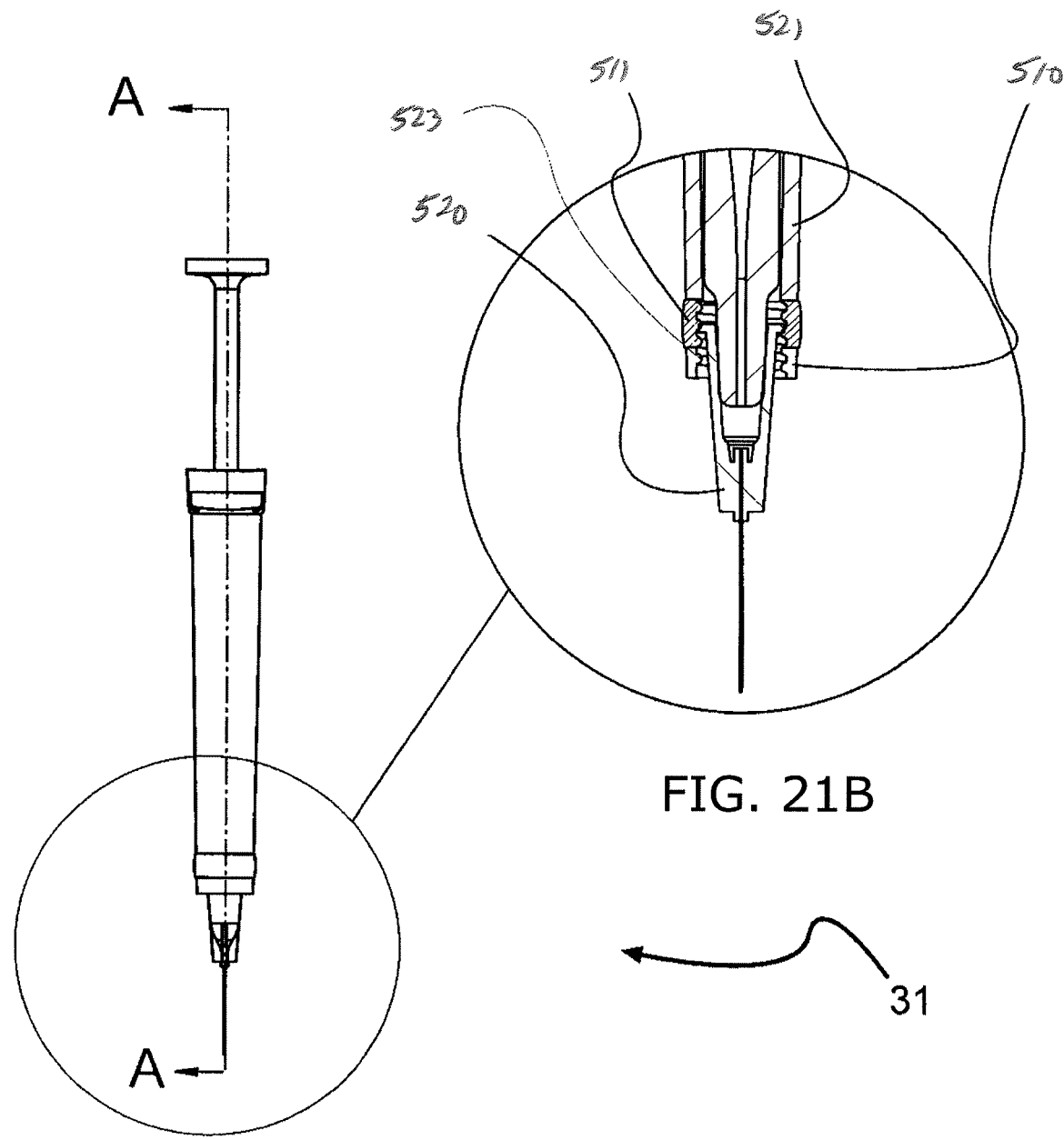
FIGS. 21A-21B, is a detailed section view of the visual indicator.

Referring to FIGS. 19A and 19B, a syringe assembly 531, can include a syringe body 521 that provides a visual indicator 511 to show that the needle 520 is properly engaged with the syringe body 521. The feature can be defined by a tinted portion of the syringe body 511 that interacts with the colored needle 520 to show that the needle is properly engaged with the syringe body 521. A cross section of the first iteration is shown in FIGS. 21A and 21B the needle body 520 is engaged with the syringe body 521 by threads 523. Clockwise motion of the needle 520 into threads 523 engages the needle 520 with syringe body 521, also seen in FIGS. 20A and 20B. An opaque portion of the syringe body 510 prevents the user from seeing the needle 520 in the visual indicator 511. When the needle 520 is visible through the transparent, tinted visual indicator 511, the needle is threaded far enough into the syringe body so as to be properly engaged with the syringe body 521. The needle 520 is made of a colored material, of a contrasting color to the transparent, tinted visual indicator 511 so as to create a visual effect such as a color change. If, for example, the needle 520 were blue and the transparent, tinted visual indicator 511 were yellow, when the needle were threaded into the syringe body 521 far enough to pass the opaque portion 510, there would be a visible green tint in the area where the needle 520 were seen through the visual indicator 511.

Figures 22A, 22B:
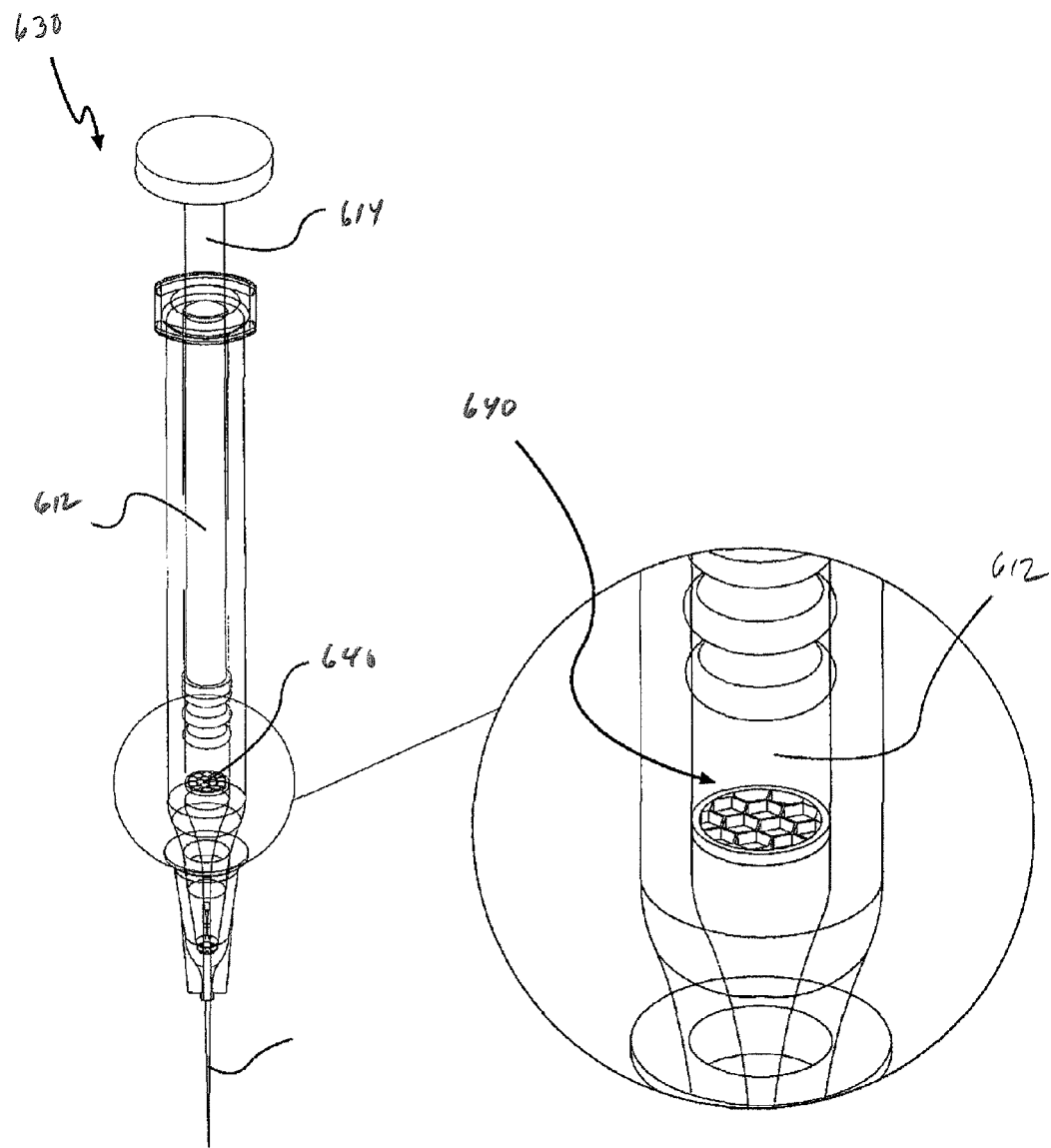
FIGS. 22A-22B, are various views of a syringe and needle/catheter flow delivery system that includes a filter located inside the body of the syringe according to the present invention.

Referring to FIG. 22, including FIGS. 22A and 22B, there illustrated is one embodiment of a flow delivery system 630 which reduces the amount of force required to transport and expel an aqueous solution of a biomaterial or a mixture of a biomaterial and a biocompatible fluid lubricant into a body at a desired location, such as, for example, the facial derma or a sphincter (i.e., urinary tract or with the esophageal tract). The biomaterial may embody collaged or other known materials used as bulking agents to augment or build up the tissue in the desired area to correct for improper sphincter operation or to cure cosmetic defects (e.g., wrinkles). The biocompatible fluid lubricant may include a non cross-linked collaged or other known materials that forma homogeneous mixture with the preferred biomaterial. Typically the amount of lubricant required in the mixture with the biomaterial is that what provides for proper intrudability of the biomaterial into the internal body tissue at the desired location and which also provides for proper extrudability of the biomaterial through and out from the flow delivery system 630.

The flow delivery system 630 may include the syringe 612, plunger 614 and needle and/or catheter 620, along with some or all of the other structural components of the previously described flow delivery systems described in detail above. In one preferred embodiment, the flow delivery system 630 also includes a filter 650 located in the flow path inside the syringe 612 such that the filter 640 covers the entire cross-sectional area of the flow path inside the syringe 612. Also, the filter is illustrated as being located in the lower portion of the syringe 612 near the tapered end 616 of the syringe 612. However, the filter 640 may be located anywhere within the flow path in the inside of the syringe 612. The filter 640 may be adhered to the inner surface of the syringe 612, or may be press fit therein. It suffices that the filter 640 be placed within the inside of the syringe 612 such that it does not move when the aqueous solution is forced through the syringe 612 by, e.g., the plunger 614.

Figure 23:
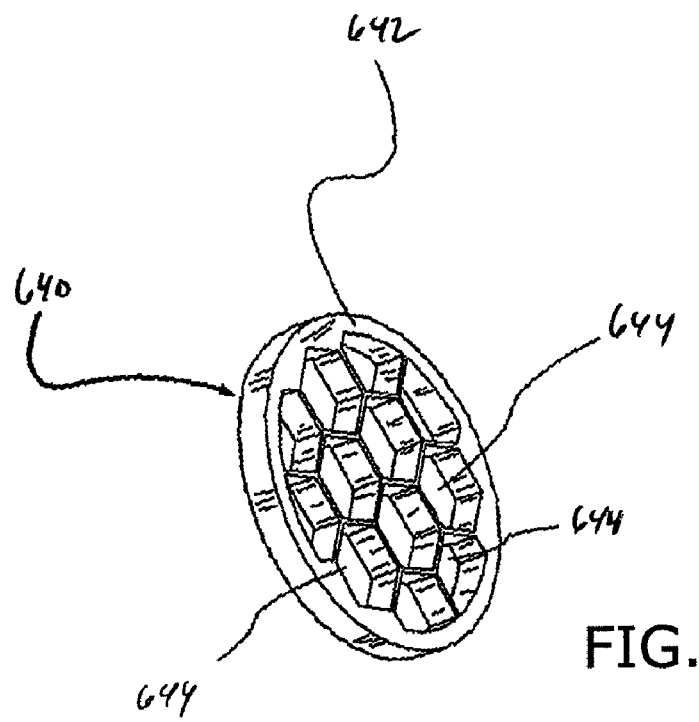
FIG. 23 is a perspective view of one embodiment of the filter of FIG. 22.

Referring to FIG. 23, there illustrated in perspective is another embodiment of the filter 640. The filter 640 comprises a disk 642 having a plurality of through holes 644 of a predetermined shape formed in the disk 642 by, e.g., an etching process. In the exemplary embodiment of FIG. 23, the disk 642 may comprise a sterile material such as stainless steel, glass or other suitable material, and the plurality of through holes 644 all have a honeycomb shape and are of equal size. In the alternative, the size of the holes 644 may vary between one another. The size of the holes 644 is preferably selected in dependence on the size of the opening or orifice in the needle and/or catheter 620 utilized in the flow delivery system 630. The holes 644 will break up or downsize any biomaterial particles within the aqueous solution which are larger than the size of the holes 644 as these particles encounter the holes when the solution travels through the syringe 612 under an applied force (e.g., from the action of the plunger 614). The downsized particles then pass through the holes 644 and through the remainder of the flow delivery system 630 and out of the needle/catheter 620 unobstructed and into a body. Also, for any particles smaller than the size of the holes, these particles pass through the holes 644 without any downsizing taking place.

Figure 24:
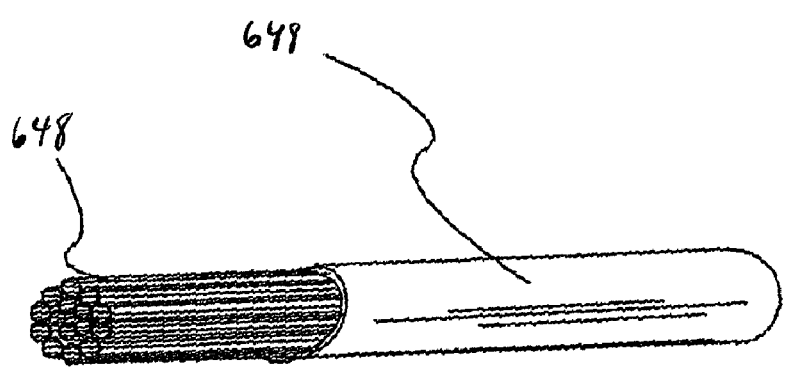
FIG. 24 is a perspective view of a bundle of glass rods prior to slicing the bundle to form a second embodiment of the filter of FIG. 22.
Figure 25:
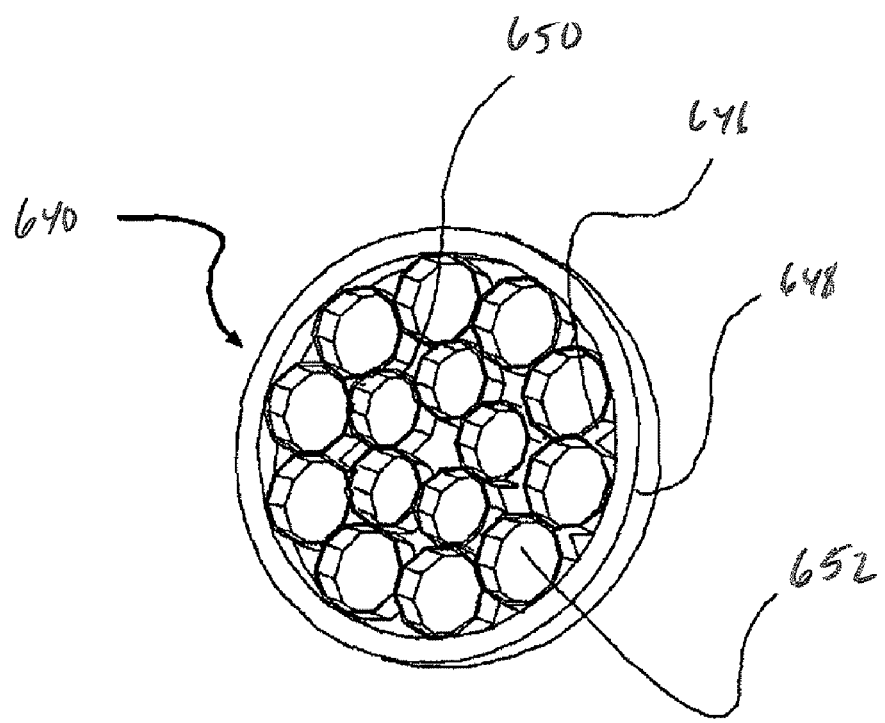
FIG. 25 is a perspective view of the second embodiment of the filter of FIG. 22.
Figure 26:
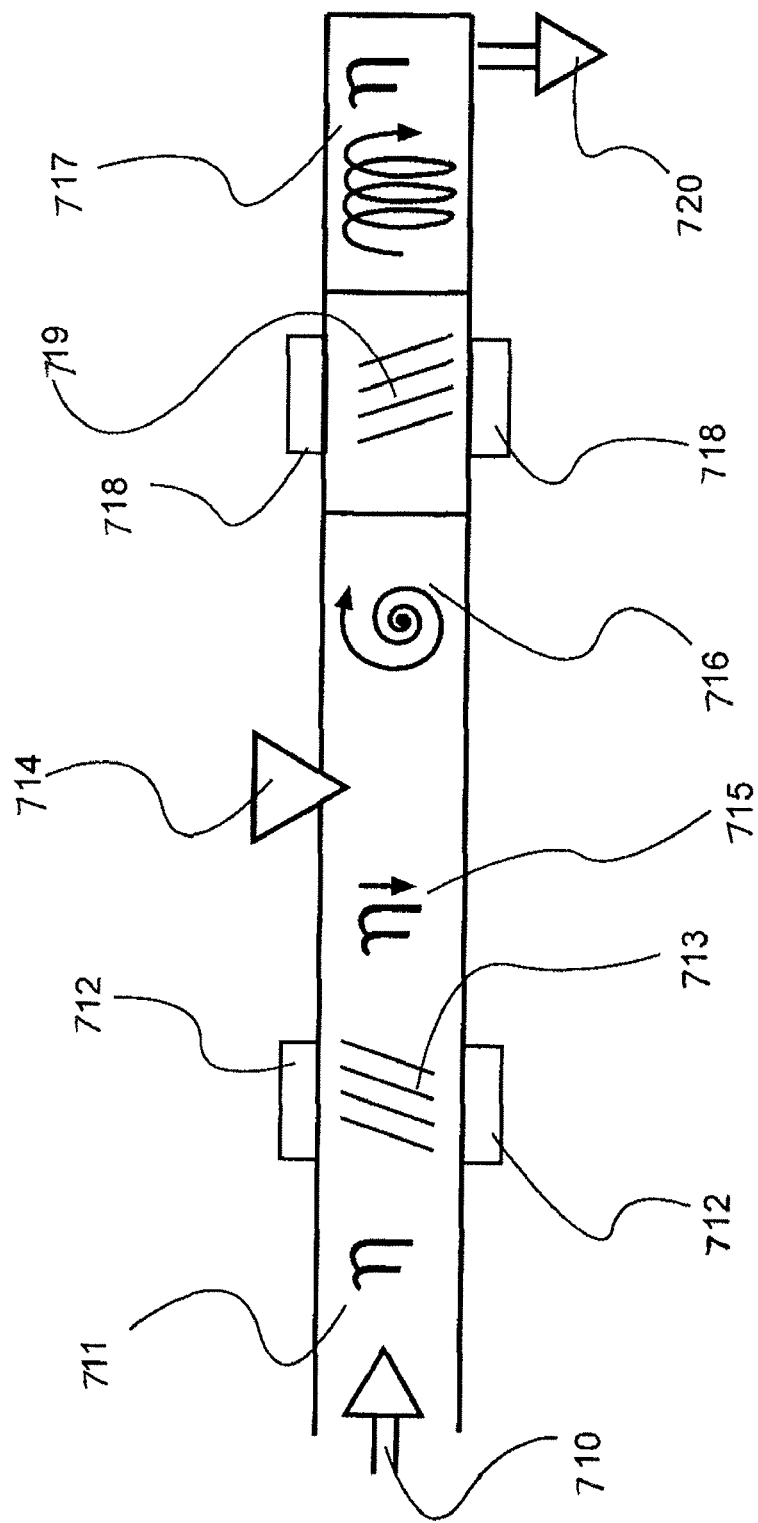
FIG. 26 is a schematic view, depicting a sterilization process.

Referring to FIGS. 24-25, there illustrated is an alternative embodiment of the filter 640. In FIG. 24, a plurality of sterile solid glass rods 646 are bundled together and held bundled together by an outer sheath 648. The sheathed bundle of rods 646 may then be sliced perpendicular to the axis of the rods 646 to form the filter 640 of FIG. 25. The spaces 650 between the glass rods function as the holes of the filter 640 for downsizing of the particles within the aqueous solution. In the alternative, some or all of the glass rods 646 comprising the filter 640 may not be solid but instead may be hollow, thereby creating an opening 652 within each of the hollow rods 646. In this alternative embodiment, the openings 652 within the hollow rods 646 are of a predetermined size for downsizing of the particles within the aqueous solution and work in conjunction with the spaces 50 between the rods 646 for downsizing of the particles.

In operation, the filter 640 within the flow delivery system 630 of the present invention breaks up any agglomerated biomaterial particle matter or mass within the aqueous solution into smaller particles of a specific size or smaller (i.e., that of the openings 644 in the filter 640 of FIG. 23). Since the size of the openings in the filter 640 is selected in dependence on the size of the orifice of the needle/catheter 620 utilized, the size of the particles suspended in the aqueous solution and transported through the syringe 612 do not clog up the needle/catheter orifice. Instead, the solution is expelled without obstruction out of the orifice of the needle/catheter 620. Thus, the flow delivery system 630 of the present invention sizes the particulate matter within the syringe 612 before it reaches the needle 620. this reduces the resistance to the flow of the aqueous solution through the flow delivery system 630, which also reduces the amount of force necessary to transport and expel the aqueous solution through the system 30 and into a body, even with systems 630 that utilize an elongate needle/catheter 20.

The flow delivery system 630 has been described for use with a conventional syringe and needle/catheter configuration that also contains a plunger 614 to supply a force to push the aqueous solution through the syringe 612 and out of the needle/catheter 620. However, the broadest scope of the present invention is not limited as such. The plunger 614 may be omitted and other means for forcing the aqueous solution through the syringe 612 may be utilized such as, for example, an acoustic transducer. Also, the syringe 612 may omit the plenum 24 (FIG. 21) and instead my employ various means for facilitating the flow of the aqueous solution out of the syringe and into and through the needles/catheter 620. For example, a contoured lower portion of the syringe 612 may be utilized.

As shown in FIG. 26, water soluble, cross-linkable polysaccharide is combined with water 710 when mixed the material is initially of high viscosity 711. The following stage of the process involves one of either or both sterilization methods 712 high-intensity, short-duration pulses of incoherent, polychromatic light in a broad spectrum; or high-amplitude ultrasonic sound waves to cause cavitation in a liquid 712 to sterilize the flowing material 713. After the sterilization process the viscosity of the material is lowered 715. While the viscosity is low, a cross-linking agent is added 714 the low viscosity permits homogenous mixing 716. The material is then sized 719 by a means of electrical and/or acoustic wave sizing 718. In order to remove air bubbles, or to de-gas the material it is placed in a vacuum and centrifuge 717, in this stage the viscosity is raised to the level prior to the sterilization. The material is then dispensed in various vessels for medical use 720.

Thus, the sterilization and sizing of biomaterial, and in particular to the sterilization and sizing of said biomaterial without the interruption of flow within the production system is provided. The same accomplishes improving the speed of the production system and the quality of the end product. The sterilization of the biomaterial can be accomplished by ultraviolet radiation and by acoustic wave. The processes may employ ultraviolet radiation, acoustic wave or both ultraviolet radiation and acoustic wave. High intensity short duration pulses of light for deactivating microorganisms may be employed along a sealed system so as to allow the process to flow without interruption or contamination. Acoustic waves may be employed as an efficient means of delivering energy into a substance. The energy may be directed in such a manner as to provide heat and pressure within a closed loop system. Acoustic and/or electrical waves may also be employed in such a manner as to provide uniform particle sizing within a bio-compatible gel. Thus, a manufacturing system can include the forming of an aqueous solution of a water soluble, cross-linkable polysaccharide; sterilizing the material with high-intensity pulses of polychromatic light and/or by the use of high-amplitude ultrasonic sound waves; initiating a cross-linking of said polysaccharide with a cross-linking agent and sizing the particles. The process continues with mixing of the cross-linking agent with the material which is then de-gassed and dispensed for medical use.

Although the present invention has been illustrated and described with respect to several preferred embodiments thereof, various changes, omissions and additions to the form and detail thereof, may be made therein, without departing from the spirit and scope of the invention.

What is claimed:

1. A syringe assembly, comprising:

a syringe body;

a leur that is contained within the syringe body;

a plunger that is movably engaged with the leur;

a needle that is engaged with the syringe body and with the leur;

one or more of a series of protrusions that permit clockwise movement of a cannula and hub assembly into a syringe body and do not permit counterclockwise movement and one or more of finger grips that are rotatably engaged with the syringe body.

2. The device of claim 1, wherein a ramp shaped protrusion is formed along a threaded distal end of a syringe body, the ramp causing interference with a cannula and hub assembly by decreasing the inner diameter in which the threads reside.

3. The device of claim 1, further comprising a means of retaining a cannula and hub assembly in the syringe body by which, in combination the hub and the syringe body engage first in a direction perpendicular to a central axis of the syringe body and secondly in direction parallel to the axis of the syringe body.

4. The device of claim 3, wherein a protrusion is provided that creates interference that prevents axial motion of the cannula and hub assembly, in the event that sufficient pressure is created in the syringe so as to disengage said hub from said syringe body.

5. The device of claim 1, further comprising a cover and container for a cannula and hub assembly engaged with the syringe body in such a manner as to protect and shield the cannula prior to, and after use that includes a torque sensitive break-away portion for proper torque engagement of the cannula hub with the syringe.

6. The device of claim 5, further comprising a means of ensuring proper engagement by providing an audible and tactile response when the proper torque and therefore proper engagement between cannula hub and syringe has been achieved.

7. The device of claim 1, further comprising a cannula and hub assembly contoured to fit the leur in such a manner as to provide an interface between the hub and leur as well as between the cannula and leur.

8. The device of claim 1, wherein the body includes an outer plastic body, a portion of said outer plastic body is transparent and tinted.

9. The device of claim 1, wherein the body includes an outer plastic body, a portion of the outer plastic body is opaque.

10. The device of claim 1, wherein the needle is colored in such a manner as to create a color change when seen through said transparent tinted portion.

* * * * *